United States Patent
Makdissi et al.

(10) Patent No.: US 11,654,290 B2
(45) Date of Patent: May 23, 2023

(54) OPTIMIZED PIEZOELECTRIC TRANSDUCER-BASED ENERGY HARVESTING MODULE, IN PARTICULAR FOR CHARGING THE BATTERY OF AN IMPLANTABLE MEDICAL DEVICE SUCH AS A LEADLESS AUTONOMOUS CARDIAC CAPSULE

(71) Applicant: CAIRDAC, Antony (FR)

(72) Inventors: Alaa Makdissi, Paris (FR); An Nguyen-Dinh, Paris (FR)

(73) Assignee: CAIRDAC, Anthony (FR)

( * ) Notice: Subject to any disclaimer, the term of this patent is extended or adjusted under 35 U.S.C. 154(b) by 99 days.

(21) Appl. No.: 17/503,716

(22) Filed: Oct. 18, 2021

(65) Prior Publication Data

US 2022/0305272 A1 Sep. 29, 2022

(30) Foreign Application Priority Data

Mar. 29, 2021 (EP) ..................................... 21315055

(51) Int. Cl.
*H02N 2/18* (2006.01)
*H10N 30/30* (2023.01)
(Continued)

(52) U.S. Cl.
CPC ......... *A61N 1/3785* (2013.01); *A61N 1/3756* (2013.01); *A61N 1/37518* (2017.08);
(Continued)

(58) Field of Classification Search
CPC .. A61N 1/057; A61N 1/37518; A61N 1/3785; H02N 2/185; H10N 30/304
See application file for complete search history.

(56) References Cited

U.S. PATENT DOCUMENTS

| 2014/0056043 | A1 | 2/2014 | Naito et al. |
| 2016/0204717 | A1* | 7/2016 | Li ........................ H02N 2/181 310/319 |
| 2019/0028041 | A1* | 1/2019 | Badel .................... H10N 30/30 |

FOREIGN PATENT DOCUMENTS

WO WO-2018220406 A1 * 12/2018 .............. H02J 1/102

OTHER PUBLICATIONS

Fang,Shengheng et al.,"An Efficient Piezoelectric Energy Harvesting Circuit With Series-SSHI Rectifier and FNOV-MPPT Control Technique", IEEE Transactions On Idustrial Electronics, IEE Service Center, vol. 68, No. 8, Jul. 10, 2020, pp. 7146-7155,XP011852436, ISSN:0278-0046.
(Continued)

*Primary Examiner* — J. San Martin
(74) *Attorney, Agent, or Firm* — Haverstock & Owens, A Law Corporation

(57) ABSTRACT

This module comprises: a circuit for interfacing with the piezoelectric beam of an oscillating pendular unit, outputting a rectified signal comprising a sequence of pulses at a frequency equal to a multiple of the oscillation frequency of the pendular unit; a buffer capacitor charged by the successive pulses outputted by the interface circuit; and a converter regulator adapted to convert a capacitor discharge current into a stabilized power supply voltage, and controlled by a feedback control stage of the Maximum Power-Point Tracking (MPPT) type. A comparator detects the conduction of a blocking diode interposed between the interface circuit and the capacitor, in order to produce a signal representative of the current value of the duty cycle of the detected conduction and non-conduction periods. This signal is compared with a predetermined optimum duty cycle value in order to enable or disable the coupling of the capacitor to the converter regulator so as to control either the capacitor discharge
(Continued)

towards an input of the converter regulator, or the continuation of its charging.

16 Claims, 15 Drawing Sheets

(51) Int. Cl.
  *A61N 1/378* (2006.01)
  *A61N 1/375* (2006.01)
  *A61N 1/05* (2006.01)
(52) U.S. Cl.
  CPC ........... *H02N 2/185* (2013.01); *H10N 30/304* (2023.02); *A61N 1/057* (2013.01)

(56) References Cited

OTHER PUBLICATIONS

Li,Shuo et al., "A Piezoelectric Energy-Harvesting System With Parallel-SSHI Rectifier and Integrated Maximum-Power-Point Tracking", IEE Solid-State Circuit Letters, IEE, vol. 2, No. 12, Dec. 1, 2019, pp. 301-304, XP011762062.
Search Report for European Patent Application No. EP21315055 dated Sep. 2, 2021.

\* cited by examiner

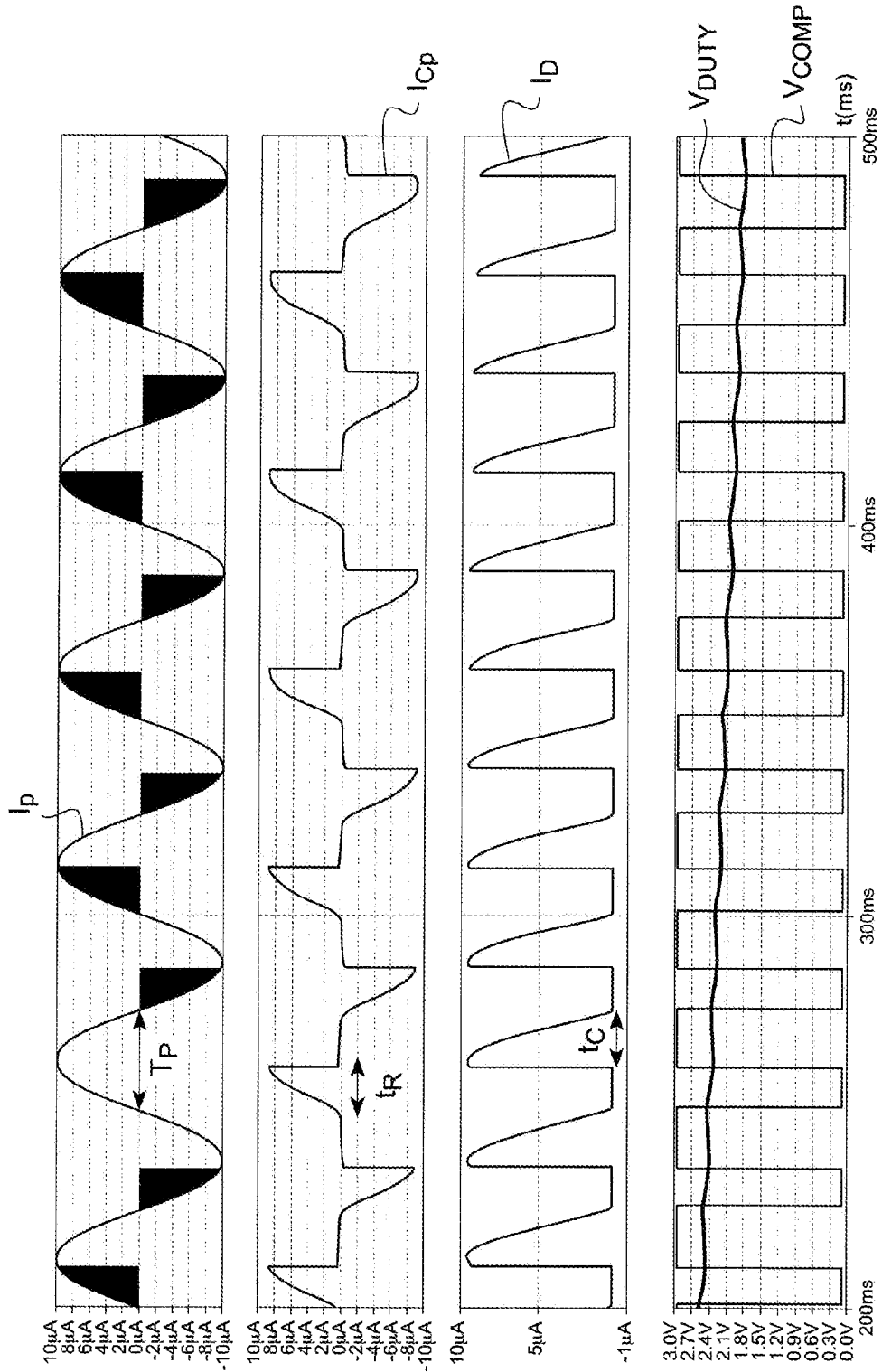

Fig.23
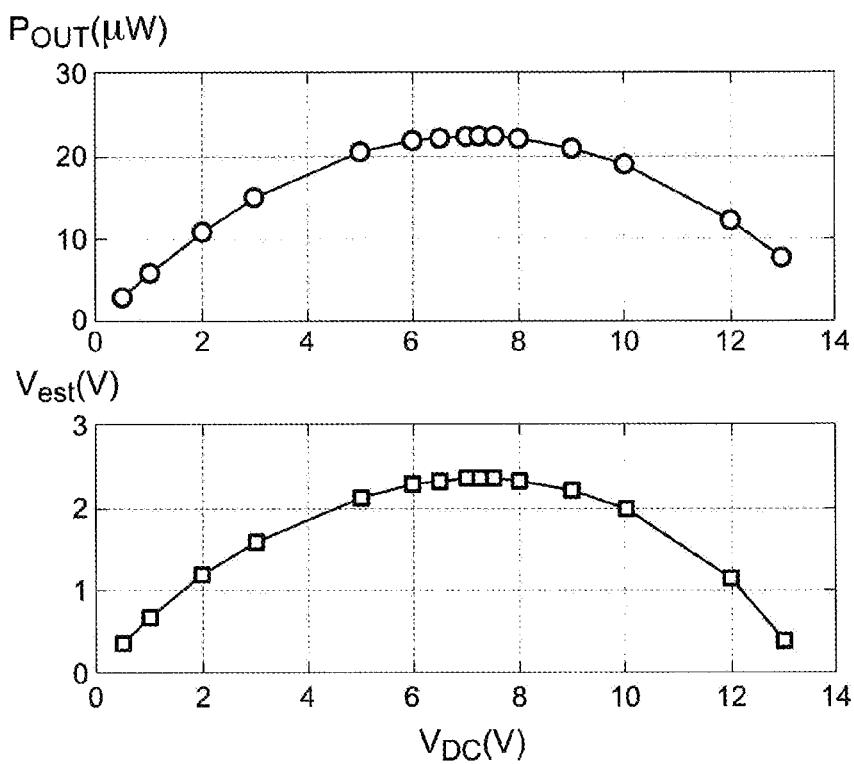
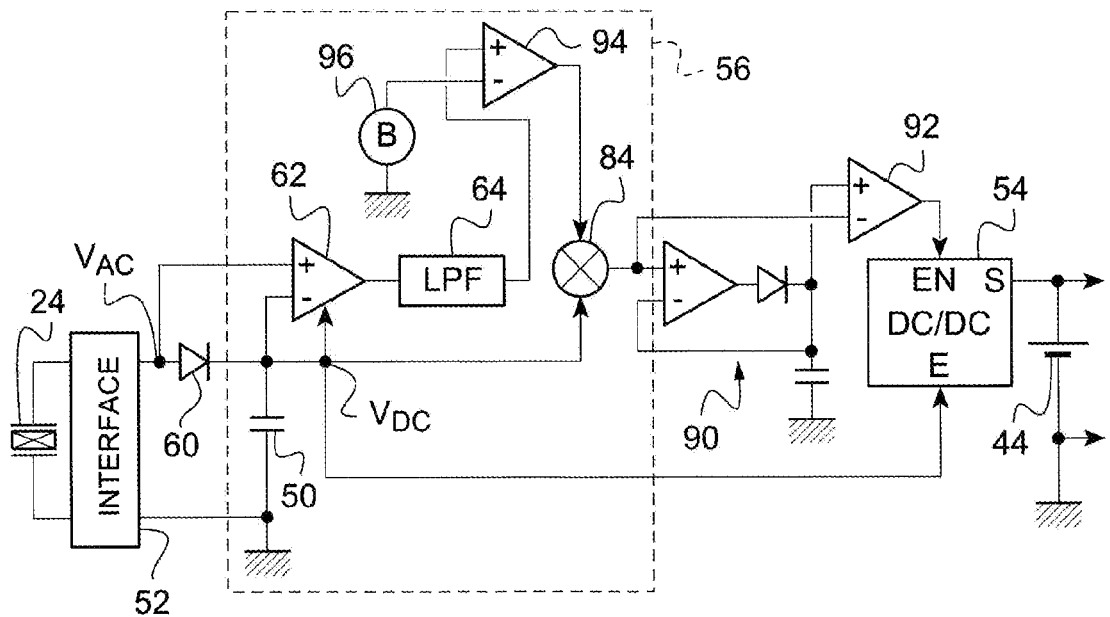
Fig.24

OPTIMIZED PIEZOELECTRIC TRANSDUCER-BASED ENERGY HARVESTING MODULE, IN PARTICULAR FOR CHARGING THE BATTERY OF AN IMPLANTABLE MEDICAL DEVICE SUCH AS A LEADLESS AUTONOMOUS CARDIAC CAPSULE

BACKGROUND OF THE INVENTION

Field of the Invention

The invention relates to energy harvesting devices, also called "harvesters" or "scavengers", which collect the mechanical energy resulting from various movements they undergo and convert this mechanical energy into electrical energy.

It more particularly relates to the harvesting devices of the so-called "PEH" (Piezoelectric Energy Harvester) type, which use as a mechanical-electrical transducer an oscillating piezoelectric beam coupled to an inertial mobile mass.

The invention will be more particularly described in an application of such energy harvesters to autonomous medical devices, in particular devices of the autonomous implantable capsule type, in particular those which are intended to be implanted in a heart cavity.

This application, although being particularly advantageous, must however not be considered as limitative of the invention, whose teachings can be applied to many other types of autonomous devices incorporating an energy harvester of the PEH type, whether these devices are implantable or not, medical or not.

Description of the Related Art

In the field of medical implants, the recent advances in miniaturization of active devices and the advances in life sciences allow from now on the development of a wide variety of fully autonomous, miniaturized implantable systems, for monitoring, diagnosis or treatment purposes. Such devices implement less invasive implantation procedures, provide more comfort, increased performances, and often open up access to new types of diagnoses and treatments.

When applied to the field of medical implants, the invention more particularly relates to those devices which incorporate a self-powering system comprising a mechanical energy harvester associated with an integrated energy storage component, such as a rechargeable battery or a high-performance capacitor.

One of the critical aspects of these miniaturized devices is the power autonomy. The life duration of such an implant being of about 8-10 years, given the very small dimensions it is not possible to use a conventional battery, even a high-density one.

The PEH harvesting device addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, heart tissue vibrations linked i.a. to closings and openings of the heart valves, or also blood flow rate variations in the surrounding environment, which stress the implant and make it oscillate at the rhythm of the flow rate variations.

The mechanical energy collected by the PEH is converted into electrical energy (voltage or current), by means of a suitable mechanical-electrical transducer, for charging the energy storage component and powering the various circuits and sensors of the device. This power supply system allows the device to operate in full power autonomy for its whole lifetime. This energy harvesting technique is particularly well adapted for powering the implanted autonomous capsules having no physical connection with a remote device. Such capsules are called for this reason "leadless capsules", for distinguishing them from the electrodes or sensors arranged at the distal end of a lead, through the whole length of which run one or several conductors connected to a generator itself connected to the opposite, proximal end.

The invention is nevertheless not limited to a particular type of capsule, nor even of leadless implant, and is applicable as well to many other types of implantable medical devices, whatever the operational purpose thereof, cardiac or other, medical or not.

In the cardiac application case, the leadless capsule continuously monitors the patient's rhythm and if necessary issues to the heart electrical pulses for pacing, resynchronization and/or defibrillation in case of rhythm disorders detected by the capsule. The capsule further comprises various electronic circuits, sensors, etc., as well as wireless communication transmission/reception means for remote exchange of data, the whole being integrated in a very small size body able to be implanted at sites of difficult access or leaving little available space, such as the ventricle apex, the inner wall of the atrium, etC.

WO 2019/001829 A1 (Cairdac) describes an example of such a leadless intracardial capsule.

The invention more particularly relates to capsules or similar implantable devices whose energy harvester is of the PEH type, i.e. using a PieZoelectric Transducer or "PZT" and an inertial pendular unit. The inertial pendular unit comprises, within the capsule body, a mobile mass called "seismic mass" or "inertial mass", which is driven according to the movements of the capsule, permanently subjected to the various external stresses described hereinabove, applied at the repetition frequency of the cardiac cycles, of the order of 60 to 120 bpm (beats per minute), i.e. of 1 to 2 Hz. After each of these stresses, the inertial mass, which is coupled to an elastically deformable element, oscillates at a natural free oscillation frequency, typically of the order of 20 Hz. The mechanical energy of the oscillation is converted into electrical energy by the PZT that is cyclically and alternately stressed in bending so as to generate within its constituent material electrical charges that are collected at the surface of the component to be used by the self-powering system of the leadless capsule. The PZT may in particular be a piezoelectric beam clamped at one end and coupled to the inertial mass at the other, free end.

The PZT output electrical signal is sent to a power management circuit of the capsule, which rectifies and regulates the electrical signal to output a stabilized direct voltage or current, usable to power the various electronic circuits and sensors of the capsule, and to charge the energy storage component.

Such a PEH energy harvesting device is described in particular in U.S. Pat. No. 3,456,134 A (Ko) and in above-mentioned WO 2019/001829 A1.

However, the electrical signal produced by the piezoelectric beam cannot be directly used to power the various electronic circuits and sensors of the capsule and charge the energy storage component (rechargeable battery or other storage means such as a high-performance capacitor, hereinafter referred to by the generic term "battery").

For that purpose, the damped oscillating electrical signal collected at the piezoelectric beam terminals is sent as an input to a power management circuit of the capsule, usually called "PMU" ("Power Management Unit"). This circuit rectifies and regulates the oscillating alternating electrical signal and outputs a stabilized voltage or current usable both to charge the battery and to power the electric circuits of the implant.

Using a PZT as a power source makes this power management particularly complex.

A first difficulty lies in the fact that the damped oscillating alternating electrical signal provided by the PZT is, from an electrical point of view, equivalent to a strongly non-linear generator, outputting an instantaneous energy that is variable and unknown, because strongly dependent on the amplitude of the beam deformations, themselves very dependent on the external stresses that cause the pendular unit to vibrate.

A second difficulty lies in the fact that, also from an electrical point of view, the PZT can be equated to an alternating current source of essentially capacitive, high internal impedance. Accordingly the voltage produced by the beam oscillations, set apart extracting supply energy from the PZT, charges the internal capacitor of the PZT, and it is then necessary to appropriately discharge the charges accumulated in the internal capacitor in order to minimize the losses by self-discharge within the PZT.

In order to maximize the power extracted by the PEH, those constraints, which are specific to the use of a PZT as a primary source of energy, led to many proposed dedicated circuit configurations, more complex than a simple full-bridge rectifier (FBR). In particular, the rectifier circuit receiving the variable voltage generated by the PZT, also called "interface circuit" of the PEH, may be a circuit of the type:

Synchronized Switch Harvesting on Inductor (SSHI) inductor- or capacitor-based Serial SSHI (S-SSHI) or Parallel SSHI (P-SSHI), or inductor- or capacitor-based Synchronous Electric-Charge Extraction (SECE), or inductor-based Single-Supply Pre-Biasing (SSPB).

These interface circuits are efficient but, due to their complexity, they cause a significant power consumption, thus at the expense of the implant autonomy. Moreover, the size of an inductor having a high quality factor, or a capacitor of sufficient capacitance, is not compatible with the extreme miniaturization required by an implantable device such as a leadless capsule.

A PEH configuration has also been proposed in which the interface circuit of the PEH (FBR or more complex circuit such as SSHI or other) charges an intermediate smoothing capacitor arranged at the input of a buck-boost DC/DC converter outputting a stabilized voltage usable to charge a battery and to power the application electric circuits downstream the battery.

Such an interface circuit with an intermediate smoothing capacitor is e.g. described by G. K. Ottman et al., Adaptive Piezoelectric Energy Harvesting Circuit for Wireless Remote Power Supply, *IEEE Transactions on Power Electronics*, 17(5):669-676, September 2002, as well as in U.S. Pat. No. 8,026,650 B2 and US 2005/285728 A1.

In this known arrangement, the voltage of the intermediate smoothing capacitor is continuously monitored, and it is discharged in a controlled manner in order to maximize the power transferred downstream the application circuits. The transferred power is however strongly dependent on the performances and internal losses of the buck-boost converter, so the energy transferred from the intermediate capacitor varies continuously as a function of the instantaneous operating point of the converter, that will have to be continuously adapted by a regulation loop taking these variations into account.

Independently of these particular difficulties of implementation, the already-proposed PEH circuits of this type are generally based on the hypothesis that the beam vibrates under the effect of a source of vibrations that is a harmonic signal of, or close to, the PZT resonance frequency, and/or it vibrates under the effect of a pulse that induces a natural harmonic vibration of the PZT.

This hypothesis corresponds to a source of vibrations consisting in stresses of relatively small amplitude but very frequent. Rather, in an application to cardiac pacing, this hypothesis is not verified. Indeed, the mechanical stresses that cause the PZT to vibrate have for origin phenomena occurring typically at the heart beat rhythm (shakes of the wall on which the implant is anchored, blood flow rate variations that make the implant oscillate, etc.). These stresses are comparable to pulse vibrations of very high amplitude, at a frequency (of the order of 1-2 Hz) that is much lower than the natural frequency of a PZT (typically of the order of 15-40 Hz).

These high amplitudes induce across the PZT a high voltage that can usually reach several tens of volts, which is much higher than the implant microbattery charging voltage, of the order of a few volts. These strong amplitudes can even significantly increase during periods of patient's stress or effort, with very high instantaneous voltage variations across the PZT, that may typically reach ±60 V in open circuit. It is then observed that the complex interface circuits described in the literature and presented as being particularly well adapted to PEH harvesters (SSHI, SECE, SSPB circuits, etC.), even combined with a buck-boost stage, have in these circumstances a poor efficiency, and, in the extreme cases, a conversion efficiency that is not much higher than that of a simple FBR with a diode bridge.

However, the power extraction efficiency is a particularly critical aspect in the case of an autonomous implant: if, for example, the application circuits of the implant require a power of 5 µW and the PEH provides only 4.8 µW (i.e. only 4% less than the required power rating), the implant will fail in the short term. De facto, any increase of the PEH efficiency, even minimal, may be essential to guarantee that the implant will operate correctly for its whole lifetime and in any circumstance.

Moreover, in addition to the electrical and extraction efficiency aspects just described, the implementation of the known PEH circuits is often incompatible with the technological requirements of the cardiac implants. For example, an interface of the inductor-based S-SSHI type generates high currents (of the order of 160 mA for an inductance of 1 mH or 320 mA for 220 µH), which are incompatible with the microbatteries used by the implants of the leadless capsule type: these microbatteries, which have a capacity of the order of 1 mAh or 2 mAh only, must in principle be charged at a current of 1 mA or 2 mA, in any case lower than 5 mA. However, if it is provided a buffer capacitor for absorbing the peaks of current and reducing the charging current to a value compatible with the small capacity of the battery, the significant additional bulk of this capacitor goes against the requirements of extreme miniaturization of the cardiac implants—the charging circuit then becoming alone more voluminous than the battery. There hence exists a need to have, in particular in a cardiac implant, a static converter circuit making it possible to (i) maximize the power extracted from a PZT subjected to stresses of high amplitude and low frequency of the heart beat type, in order to (ii) send a continuous and stabilized voltage to a battery and to the various electric circuits of the implant, by minimizing the conversion losses, and (iii) by respecting the requirements of extreme miniaturization of the medical implants, especially the leadless capsules.

BRIEF SUMMARY OF THE INVENTION

The object of the invention is to propose a PEH configuration that addresses the multiple drawbacks and constraints exposed hereinabove. For that purpose, the invention proposes an energy harvesting module comprising, in a per se known manner, a pendular unit subjected to external stresses applied to the module, the pendular unit comprising a beam that is elastically deformable in bending according to at least one degree of freedom, with a clamped end and an opposite free end coupled to an inertial mass. The beam is a piezoelectric beam forming a mechanical-electrical transducer adapted to convert a mechanical energy produced by oscillations of the pendular unit into an oscillating alternating electrical signal collected by electrodes of the beam. A power management circuit rectifies and regulates the signal collected by the electrodes, whereby outputting a stabilized power supply direct voltage or current.

This power management circuit comprises: an interface circuit coupled to the piezoelectric beam, receiving as an input the oscillating alternating electrical signal provided by the piezoelectric beam and outputting a rectified signal comprising a sequence of pulses at a frequency equal to a multiple of the oscillation frequency of the pendular unit; at the output of the interface circuit, a buffer capacitor charged by successive pulses provided by the interface circuit; a converter regulator adapted to convert a buffer capacitor discharge current into said stabilized power supply direct voltage or current; and a circuit for controlling the converter regulator, comprising a feedback control stage of the Maximum Power-Point Tracking, MPPT, type, based on an estimate of a power extracted from the piezoelectric beam.

Characteristically of the invention, the MPPT feedback control stage is controlled by a current value of a direct or reverse duty cycle of the pulses outputted at a frequency equal to a multiple of the oscillation frequency of the pendular unit at the output of the interface circuit.

In a preferential embodiment, the power management circuit further comprises a blocking diode interposed between the interface circuit and the buffer capacitor, and the MPPT feedback control stage comprises a circuit for detecting conduction periods of the blocking diode, an extraction circuit adapted to produce a signal representative of a current value of the duty cycle based on conduction and non-conduction periods detected by the detection circuit, and a circuit for comparing the current value of the duty cycle with a predetermined optimum duty cycle value.

The MPPT feedback control stage can then in particular further comprise a control circuit, for: i) if the current duty cycle value is higher than the optimum duty cycle value, coupling the buffer capacitor to the converter regulator so as to discharge the buffer capacitor towards an input of the converter regulator, or ii) if the current duty cycle value is lower than the optimum duty cycle value, uncoupling the buffer capacitor from the converter regulator so as to allow the charging of the buffer capacitor by the successive pulses outputted by the interface circuit to continue.

The converter regulator can in particular be a step-up/step-down switching regulator of the buck-boost type, which can be selectively enabled/disabled by the control circuit.

According to various advantageous implementations of the above-mentioned preferential embodiment:
  the conduction period detection circuit and the extraction circuit comprise a comparator coupled at an input to the blocking diode, adapted to detect the polarity of the potential difference across the blocking diode and, downstream from the comparator, a low-pass filter outputting a signal representative of the current duty cycle value;
  the interface circuit comprises a full-bridge rectifier, FBR, circuit, with a diode bridge or a MOSFET-based negative voltage converter, NVC, and the predetermined optimum duty cycle value is between 50% and 55% in terms of direct duty cycle, or between 45% and 50% in terms of reverse duty cycle;
  the interface circuit comprises a synchronized discharge switching FBR circuit, FBR-SO, and the predetermined optimum duty cycle value is between 50% and 52% in terms of direct duty cycle, or between 48% and 50% in terms of reverse duty cycle;
  the interface circuit comprises a synchronized parallel discharge inductor switching FBR circuit, P-SSHI, and the predetermined optimum duty cycle value is between 52% and 60% in terms of direct duty cycle, or between 40% and 48% in terms of reverse duty cycle;
  the MPPT feedback control stage comprises: a first comparator comparing voltages across the blocking diode; downstream from the first comparator, a low-pass filter outputting a signal representative of a current value of the reverse duty cycle; and a second comparator comparing a signal outputted by the low-pass filter with a voltage reference, and outputting a signal for controlling the converter regulator;
  the MPPT feedback control stage comprises: a first comparator comparing voltages across the blocking diode; downstream from the first comparator, a first low-pass filter outputting a first signal representative of a current value of the direct duty cycle and of a voltage outputted by the interface circuit; a Schmitt trigger receiving the signal outputted by the first comparator; downstream from the Schmitt trigger, a second low-pass filter outputting a second signal representative of a current value of the direct duty cycle; and a multiplier combining the signals outputted by the first and the second low-pass filters, respectively, and outputting a signal representative of an estimate of a power extracted from the piezoelectric beam;
  the MPPT feedback control stage comprises: a first comparator comparing voltages across the blocking diode; downstream from the first comparator, a low-pass filter outputting a first signal representative of a current duty cycle value and of a level of a voltage outputted by the interface circuit; downstream from the low-pass filter, a second comparator comparing the signal outputted by the low-pass filter with a voltage reference, and outputting a signal that is function, but with an offset, of a current value of the direct duty cycle; and a multiplier combining the signal outputted by the second comparator and a voltage signal across the buffer capacitor, and outputting a signal representative of an estimate of a power extracted from the piezoelectric beam;
  in the last two cases, it can be further provided an envelope detector receiving as an input the signal representative of an estimate of the power extracted from the piezoelectric beam, outputted by the multiplier.

The module according to the invention can in particular be incorporated to an autonomous device including within a device body: an electronic unit; said power harvesting module; and an energy storage component for powering the electronic unit. The stabilized direct voltage or current provided by the power management circuit is then used to power the electronic unit and/or to charge the energy storage component of the autonomous device.

In particular, this autonomous device can be an active medical device, such as an implantable autonomous capsule comprising a capsule body with an anchoring element for anchoring it to a wall of a patient's organ. The external stresses to which is subjected the pendular unit of the energy harvesting module are stresses applied to the capsule body under the effect of movements of said wall and/or blood flow rate variations in the surrounding environment.

BRIEF DESCRIPTION OF THE DRAWINGS

An exemplary embodiment of the present invention will now be described with reference to the appended drawings, in which the same references denote identical or functionally similar elements throughout the figures.

FIG. 8 illustrates the instantaneous variations of the various electrical values and signals of the circuit of FIG. 7 in the case where the interface circuit is a simple full-bridge rectifier FBR, as well as the parameters defining the duty cycle.

FIG. 23 is a comparative representation of the curves of estimated power and extracted power effectively measured, obtained with the circuits of FIG. 22.

FIG. 24 illustrates an alternative embodiment of the PEH circuits of FIG. 22, operating more precisely.

DETAILED DESCRIPTION OF A PREFERRED EMBODIMENT OF THE INVENTION

Application to a Cardiac Implant of the Leadless Capsule Type

An exemplary embodiment of the device of the invention will now be described, in an application to an autonomous implantable capsule intended to be implanted into a heart cavity.

As indicated hereinabove, this particular application is not limitative of the invention, whose teachings can be applied to many other types of autonomous devices incorporating an energy harvester of the PEH type, whether these devices are implantable or not, medical or not.

Figure 1:
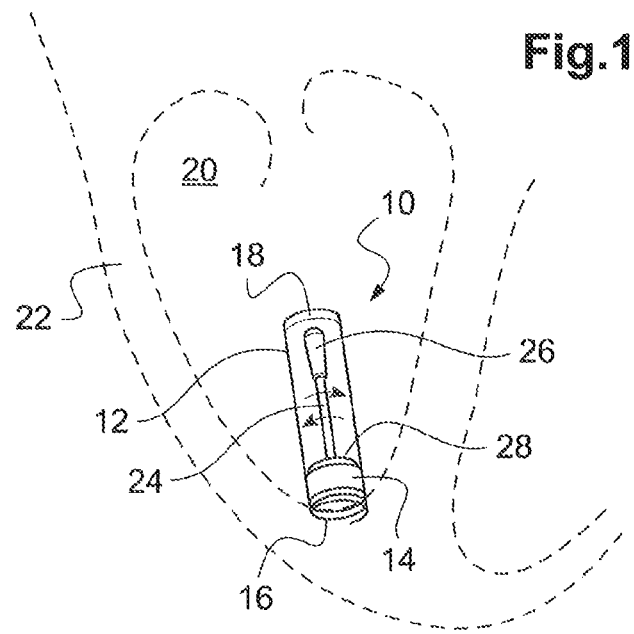
FIG. 1 illustrates a medical device of the leadless capsule type in its environment, implanted in the bottom of the right ventricle of a patient.

FIG. 1 shows a leadless capsule device 10 in an application to cardiac pacing.

Capsule 10 has the external form of an implant with an elongated cylindrical tubular envelope 12 enclosing the various electronic and power supply circuits of the capsule, as well as a pendular unit based energy harvester. The typical size of such a capsule is about 6 mm diameter for about 15-40 mm length.

Tubular envelope 12 has, at its front (distal) end 14, a protruding anchoring element, for example an helical screw 16, to hold the capsule on the implantation side. Other anchoring systems can be used, and do not change in any way the implementation of the present invention. The opposite (proximal) end 18 of capsule 10 is a free end, which is only provided with means (not shown) for the temporary connection to a guiding catheter or other accessory used for implantation or explanation of the capsule, which is then detached from the latter.

In the example illustrated in FIG. 1, leadless capsule 10 is an endocavitary implant implanted into a cavity 20 of myocardium 22, for example at the apex of the right ventricle. As an alternative, still in an application to cardiac pacing, the capsule can also be implanted on the interventricular septum or on an atrial wall, or also be an epicardial capsule placed on an external region of the myocardium, these different implantation modes not changing in any way the implementation of the present invention. To perform the detection/pacing functions, an electrode (not shown) in contact with the heart tissue at the implantation site collects the heart depolarization potentials and/or applies pacing pulses. In certain embodiments, the function of this electrode can be provided by anchoring screw 16, which is then an active screw, electrically conductive and connected to the detection/pacing circuit of the capsule.

Leadless capsule 10 is moreover provided with an energy harvesting module, so-called "PEH", comprising an inertial pendular unit that oscillates, inside the capsule, following the various external stresses to which the capsule is subjected. These stresses may result in particular from: movements of the wall to which the capsule is anchored, which are transmitted to tubular body 12 by anchoring screw 16; and/or blood flow rate variations in the environment surrounding the capsule, which produce oscillations of tubular body 12 at the rhythm of the heartbeats; and/or various vibrations transmitted by the heart tissues.

The pendular unit is consisted by a piezoelectric beam 24 clamped at one of its ends, at position 28, and whose opposite, free end is coupled to a mobile inertial mass 26. Piezoelectric beam 24 is an elastically deformable flexible beam that constitutes, with inertial mass 26, a pendular system of the mass-spring type. Due to its inertia, mass 26 subjects beam 24 to a deformation of the vibratory type on either side of a neutral or non-deformed position corresponding to a stable rest position in the absence of any stress.

Actually, as for its mechanical behavior, this unit may be equated to a "fixed/free beam" structure, having a natural oscillation frequency which is in the present case the frequency at which the mass/spring system oscillates. It will be noted that this natural oscillation frequency, typically of the order of a few tens of hertz, is noticeably higher than the frequency of the external cyclic stresses that correspond to the heartbeat frequency (at the most a few hertz). Hence, at each heart contraction, the inertial mass (or other functionally similar mechanical component) will be stressed with a higher or lower amplitude, then the pendular system will oscillate several times with decreasing amplitudes (bounces characteristic of a damped periodic oscillation), and will finally stabilize up to the following heartbeat, where the stress/oscillation cycle will be comparably repeated.

Beam 24 further performs a mechanical-electrical piezoelectric transducer (PZT) function for converting into electrical charges the mechanical bending stress that is applied to it. These charges are collected by electrodes at the surface of the beam to produce an electrical signal that, after rectification, stabilization and filtering, will power the electronic circuits of the capsule.

Figure 2:
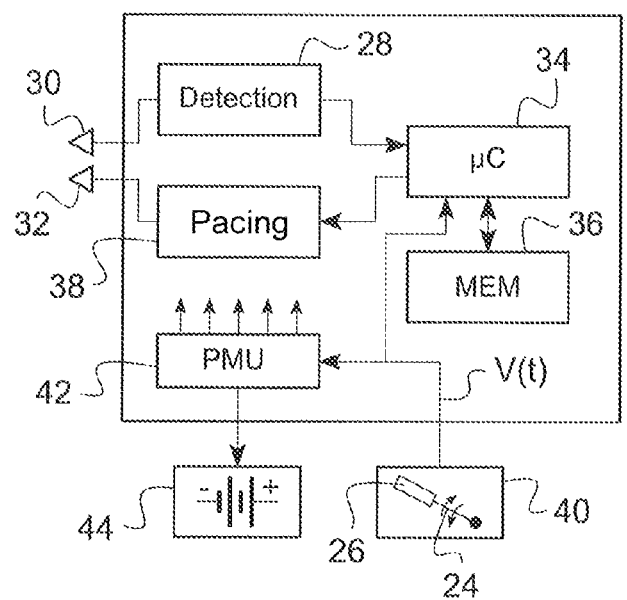
FIG. 2 schematically shows the main functional blocks constituting the leadless capsule.

FIG. 2 is a synoptic view of the various electric and electronic circuits integrated to the leadless capsule, presented as functional blocks.

Block 28 denotes a heart depolarization wave detection circuit, which is connected to a cathode electrode 30 in contact with the heart tissue and to an associated anode electrode 32, for example a ring electrode formed on the tubular body of the capsule. Detection block 28 comprises filters and means for analog and/or digital processing of the collected signal. The resulting processed signal is applied to the input of a microcomputer 34 associated with a memory 36. The electronic unit also includes a pacing circuit 38 operating under the control of microcomputer 34 to issue, as needed, to the electrode system 30, 32 myocardial pacing pulses.

It is moreover provided an energy harvesting circuit or PEH 40, consisted by the pendular unit formed by piezoelectric beam 24 and inertial mass 26, described hereinabove with reference to FIG. 1. As piezoelectric beam 24 also ensures a mechanical-electrical transducer function, it converts into electrical charges the mechanical stresses undergone and produces a variable electrical signal V(t), which is an alternating signal oscillating i) at the natural oscillation frequency of the pendular beam 24/mass 30 unit, and ii) at the rhythm of the successive beats of the myocardium to which the capsule is coupled.

The variable electrical signal V(t) is sent to a power management circuit or PMU 42. PMU 42 rectifies and regulates the signal V(t) so as to output a stabilized direct voltage or current serving to power the various electronic circuits and to charge the integrated microbattery 44.

Figure 3:
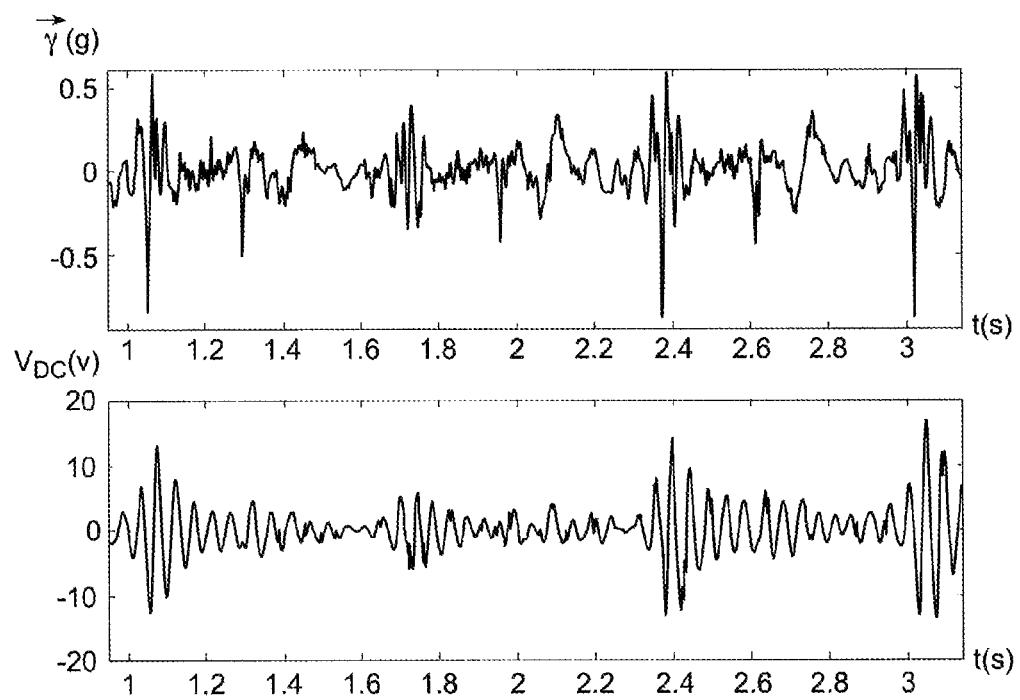
FIG. 3 is an exemplary chronogram showing, on a sequence of heart beats, the instantaneous variations of the acceleration undergone by the leadless capsule with, opposite, the corresponding variations of the open-circuit voltage across the PZT, produced by the oscillations of the pendular unit of the PEH, for a situation corresponding to a patient's resting or low activity state.

FIG. 3 is an exemplary chronogram showing, in a sequence of heart beats, the instantaneous variations of the acceleration undergone by the leadless capsule with, opposite, the corresponding variations of the open-circuit voltage $V_{OC}$ across the PZT, produced by the oscillations of the PEH pendular unit, for a situation corresponding to a patient's resting or low activity state.

This voltage $V_{OC}$ is in the form of a recurrent signal repeating at the rhythm of the successive heart beats, with a sequence of damped sinusoidal oscillations comprising a first peak of high amplitude followed with a sequence of "bounces" of decreasing amplitudes, which go on up to a new contraction of the myocardium producing similar variations of the voltage. The order of magnitude of the repetition frequency of the cardiac cycles is typically of 1 to 2 Hz (60 to 120 bpm). The natural frequency of the pendular unit is determined by the geometry of beam 24 (mainly its length and thickness), by the elasticity of the material of which it is composed, and by the mass of inertial mass 28. This natural frequency of free oscillations has a far higher value than the cardiac rhythm frequency, typically a frequency of the order of 15 to 40 Hz.

In this situation, for moderate accelerations (typically a fraction of g), the open-circuit voltage $V_{OC}$, i.e. in the absence of load corrected to the PZT terminals, varies in a range of the order of ±12 V in the example illustrated.

Figure 4:
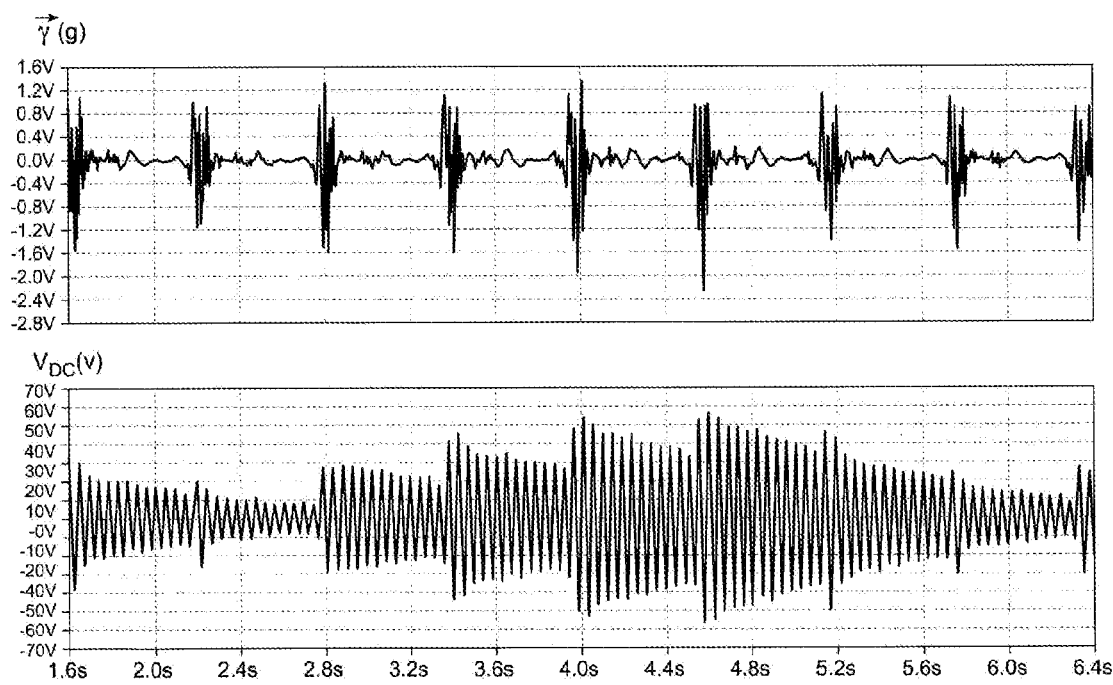
FIG. 4 is similar to FIG. 3, in a situation corresponding to a patient's stress or intense effort state, leading to far higher acceleration and voltage levels than in the case illustrated in FIG. 3.

On the other hand, as illustrated in FIG. 4, in a situation corresponding to a patient's stress or intense effort state, instead of a static position or a moderate effort. The accelerations can then reach 2 g, leading to a voltage $V_{OC}$ able to vary from ±5 V to ±60 V peak-to-peak.

General Principle of an MPPT Feedback-Control Energy Harvester

Figure 5:
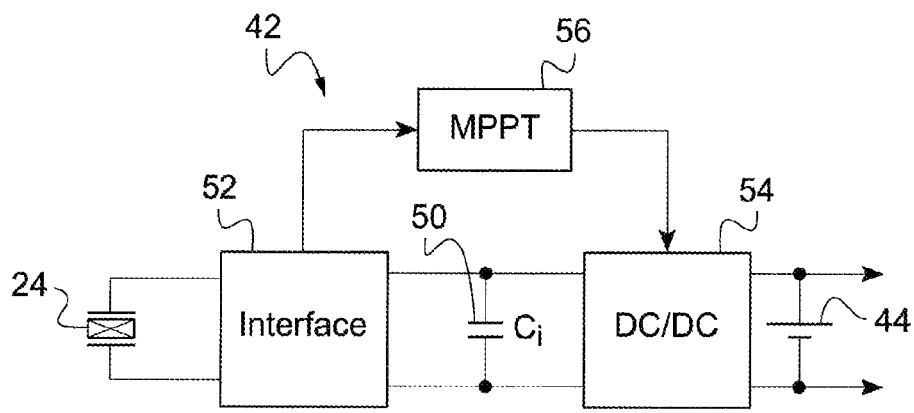
FIG. 5 is a synoptic view of a PMU circuit with an intermediate capacitor, circuit to which are applied the teachings of the invention.

FIG. 5 is a synoptic view of a PEH harvesting circuit with an intermediate capacitor, according to an overall per se known configuration, for example from Ottman's article and U.S. Pat. No. 8,026,650 B2 and US 2005/285728 A1 mentioned in the introductory section.

This arrangement comprises an intermediate smoothing capacitor 50, of capacitance $C_i$, charged by an interface circuit 52 interposed between PZT 24 and intermediate capacitor 50.

Interface circuit 52 collects the damped oscillating alternating electric signal produced by PZT 24 and outputs a rectified voltage for charging intermediate capacitor 50. In its simplest form, interface circuit 52 is a diode-bridge FBR, but other more complex circuits can be used to optimize the extraction of the energy produced by the PZT, in particular an interface circuit of the SSHI type.

Intermediate capacitor 50 makes it possible to smooth the variations of the rectified voltage, which is applied to the input of a direct-direct (DC/DC) converter 54, typically of the buck-boost type, so as to output a voltage stabilized at a level allowing the charging of battery 44 and the powering of the circuits located downstream of this battery.

To optimize the power extraction, a feedback control stage 56 of the Maximum Power-Point Tracking (MPPT) type controls buck-boost converter 54 so as to maximize the transfer towards battery 44 of the energy accumulated on capacitor 50.

However, the conventional MPPT feedback controls, even if they are adapted to the energy harvesting by a PEH, do not allow answering the multiple constraints mentioned hereinabove, peculiar in particular to the miniaturized cardiac implants such as the leadless capsules.

Figure 6:
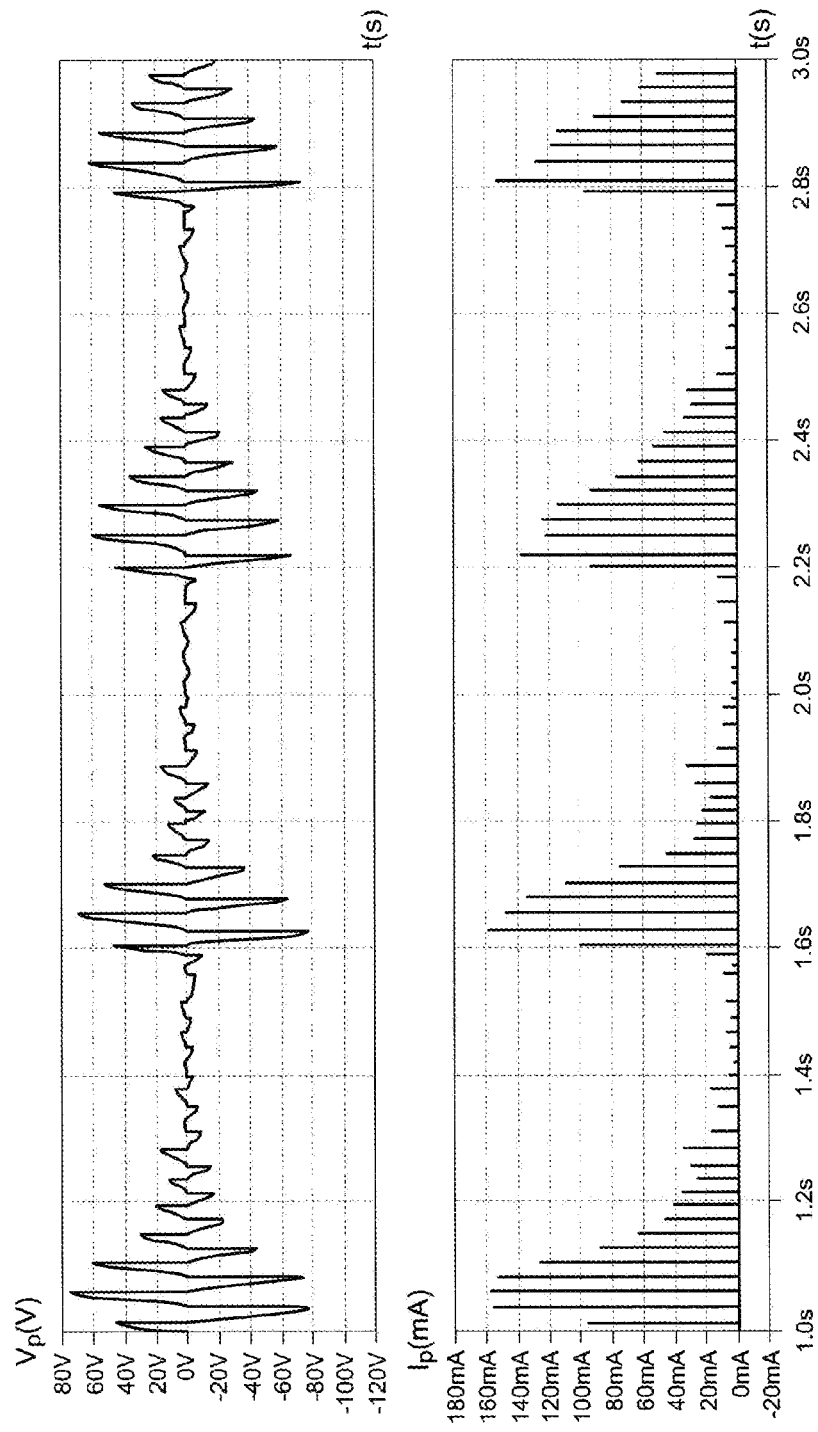
FIG. 6 is an exemplary chronogram of the variable voltages and currents produced by a PMU circuit of the type of that shown in FIG. 5, in a known configuration in the absence of application of the teachings of the invention.

Firstly, the use of interface circuits 52 of the conventional S-SSHI or SECE type, incorporating an inductor for the transfer to the battery of the voltage produced by the PZT, is not compatible with the charging of microbatteries such as those used in the leadless implants, whose low capacity limits the maximum charging current to a value of the order of 5 mA. Indeed, with reference to FIG. 6 that is an exemplary chronogram of the variable voltages and currents produced by a PMU circuit of the type of that shown in FIG. 5, in a known configuration in the absence of application of the teachings of the invention, it is observed that the voltage across the PZT can reach up to ±60 V, which leads, at the time of the inductor switch, to an extremely high output current, that may typically reach 160 mA for an inductance of 1 mH.

Secondly, with a signal such as that produced by a PZT incorporated to the leadless capsule, the periodicity of the heart beats (1 to 2 Hz) is very far from the harmonic frequency of the PZT (of the order of 15 to 40 Hz), which does not allow a precise and instantaneous optimization of the transfer of energy by the MPPT feedback control.

Thirdly, the known MPPT feedback controls operate according to techniques implementing relatively slow and energy-consuming algorithms. These algorithms are usually of the Perturbate-and-Observe (P&O) type, consisting in causing an offset of the output voltage and measuring the power variation observed to adjust the output voltage to a level maximizing this power, or of the Fractional Open-Circuit (FOC) type, consisting in temporary disconnecting the converter from the intermediate capacitor, then measuring the voltage across the latter in open circuit and adjusting the voltage to a value corresponding to half this open-circuit voltage, a value supposed to correspond to the maximum output power. In either case, to find the direction in which the output voltage must be changed, the algorithm causes a temporary power loss of the system by forcing the latter to operate out of its optimum range. That way to proceed is difficult to envisage in the case of a cardiac implant where, ideally, the adjustment of the power transfer must be made at each cardiac cycle, and by minimizing the energy losses specific to the feedback control, at the risk of not charging the microbattery sufficiently.

Indeed, during a same cardiac cycle, the open-circuit voltage $V_{OC}$ of the PZT may vary by about 5 to 24 volts, corresponding to an optimum value $V_{DC}$ of 2.5 to 12 volts for an optimum set to $V_{OC}/2$. An MPPT feedback control algorithm that would operate on the basis of the measurement of the open-circuit voltage $V_{OC}$ should operate several measurements of $V_{OC}$ during a same cardiac cycle to follow efficiently the point of optimum operation of output power. Indeed, the output power can vary during a same cardiac cycle between about 2 µW and 50 µW, so that the set point of the feedback control varies continuously, imposing a very high number of measurements to obtain a really efficient feedback control.

Principle of the Invention and Extraction of the Duty Cycle Information

The present invention proposes another technique for maximizing the extraction of the energy produced by the PZT, that will now be described with reference to FIGS. 7 to 21.

The principle of the invention consists in (i) deriving directly a signal representative of a cyclic conduction ratio (duty cycle) from signals directly available at the interface with the PZT, and (ii) dynamically controlling the MPPT feedback control based on this duty cycle value.

Figure 7:
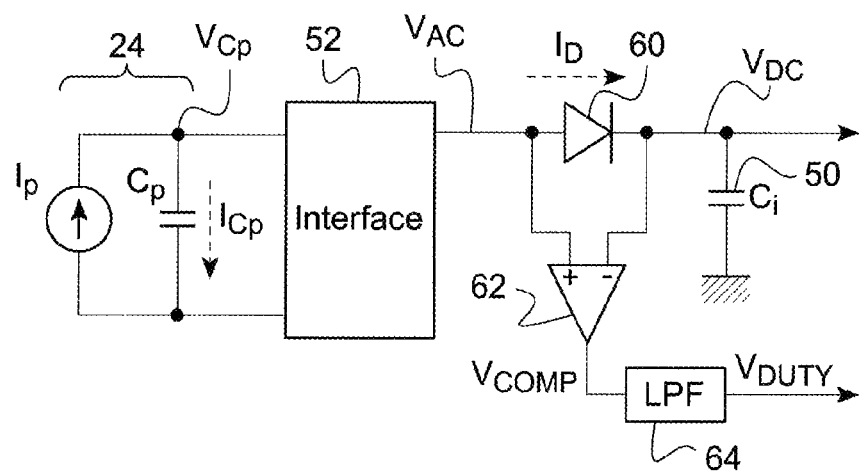
FIG. 7 is a principle representation of a circuit making it possible, according to the invention, to derive directly a signal representative of a conduction duty cycle based on signals available at the interface with the PZT.

FIG. 7 schematically describes the way to detect the conduction and non-conduction periods of a diode connected at the output of a PMU interface circuit such as that of FIG. 5, and to derive therefrom a instantaneous current duty cycle value.

Interface 52 provides a voltage $V_{AC}$, which is for example a voltage simply rectified by a full-bridge rectifier FBR. This voltage $V_{AC}$ is applied to the anode of a blocking diode 60 whose cathode is linked to intermediate capacitor 50, by hence applying to the latter a charging voltage when diode 60 is in the conductive state. The voltage across capacitor 50, rectified and filtered by the capacitance $C_i$ of this capacitor 50, is a filtered and substantially continuous voltage $V_{DC}$.

Current $I_D$ passing through the diode produces between the terminals of the latter a voltage drop equal to the direct voltage of the diode. The corresponding voltage difference is detected by a comparator 62 whose inputs are connected to the respective terminals of diode 60. Output $V_{COMP}$ of comparator 62 is applied to a low-pass filter LPF 64 outputting a signal $V_{DUTY}$.

FIG. 8 illustrates a sequence of chronograms taken at different points of the circuit of FIG. 7 during six successive cycles of vibration of the PZT, taken during a same cycle of mechanical stress of the PEH, in particular during a same heart beat of the implant worn by the patient.

The PZT oscillations produce, by piezoelectric effect, a current $I_P$ (first chronogram of FIG. 8) of approximately sinusoidal shape and half-period $T_P$. At the beginning of the variation, current $I_P$ charges the PZT internal capacitance $C_p$ (represented on the equivalent diagram of FIG. 7), up to a voltage $V_{AC}$. The charging current $I_{Cp}$ (second chronogram of FIG. 8) generated inside the PZT and charging the internal capacitance $C_p$ increases for a dead time duration $t_R$ (dark area on the sinusoid of the first chronogram) during which the voltage $V_{AC}$ is not sufficient to put diode 60 in conduction ($V_{AC} < V_{DC}$).

When $V_{AC}$ reaches the level of voltage $V_{DC}$ across intermediate capacitor 50, diode 60 enters into conduction and is flown through by a current $I_D$ (third chronogram of FIG. 8), this conduction continuing for a duration $t_C$ up to the next zero-crossing of current $I_D$.

As can be seen in the figure, the conduction duration $t_C$ is relatively long for the first oscillation cycles of the PZT, then progressively decreases during the following cycles, and will continue to decrease until the next heart beat that will mechanically stress the PZT again.

Comparator 62 correspondingly outputs a signal $V_{COMP}$ (fourth chronogram of FIG. 8) in the form of pulses alternating between a high level corresponding to a conductive state of diode 60 ($V_{AC} > V_{DC}$) and a low level corresponding to a non-conductive state of diode 60 ($V_{AC} < V_{DC}$). The duration of the pulses at the high level (conductive state of the diode) reduces progressively over the successive oscillation cycles of the PZT, and the filtered value $V_{DUTY}$ of the pulse signal $V_{COMP}$ gives a continuous, non-impulse, representation of this progressive decreasing.

More precisely, the mean value of the filtered output signal $V_{DUTY}$ is representative of a measurement of the duty cycle $\alpha = t_C/T_P$, defined as the ratio between the period $t_C$ during which the diode is conductive and the half-period of natural oscillation $T_P$ of the PEH. In the same way, the reverse duty cycle $\beta = t_R/T_P$ is defined as the ratio between the period $t_R$ during which the diode is blocked and the half-period of natural oscillation $T_P$ of the PEH. The measurement of the reverse duty cycle $\beta$ can be made by reversing the two inputs of the comparator.

Use of the Duty Cycle Information

These parameters $\alpha$ or $\beta$ will be used thereafter to control the MPPT feedback control of the PEH, whose operating point will be dynamically optimized to maximize the power extracted from the PZT.

Figure 9:
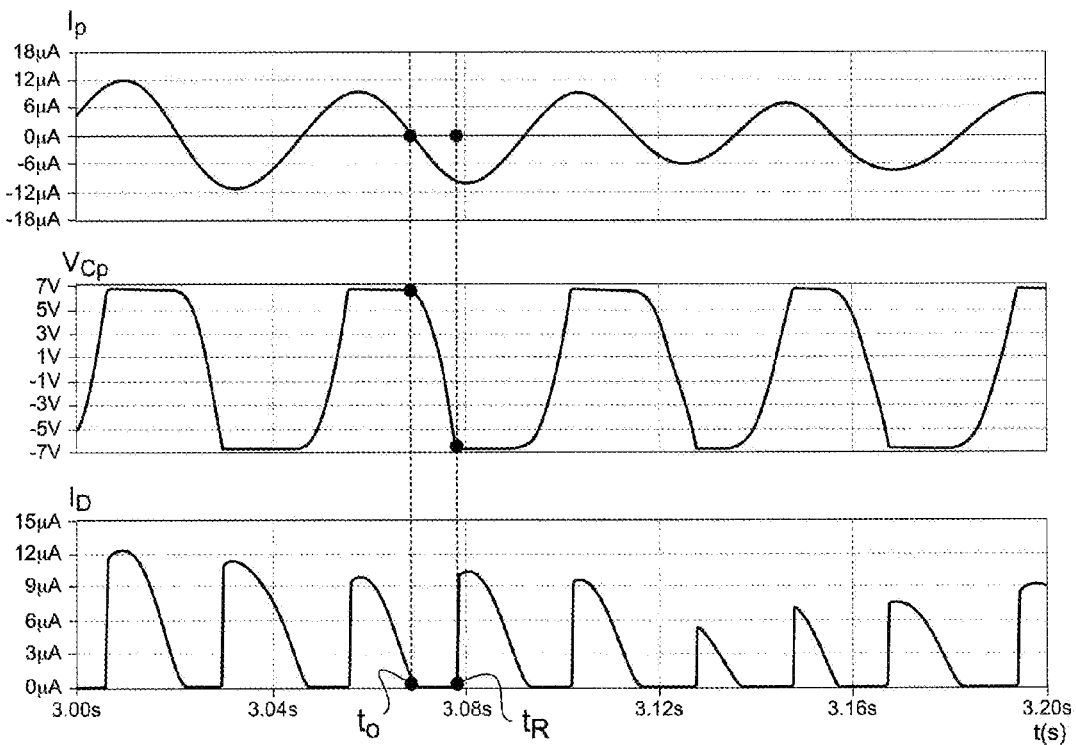
FIG. 9 illustrates, in the case of an interface circuit consisted of a simple full-bridge rectifier, a chronogram of the variations of various signals taken on the circuit of FIG. 7 during successive oscillations of the PZT in a same heart beat.

FIG. 9 illustrates, on a respective series of curves taken in a configuration in which the interface circuit 52 is a simple diode-bridge FBR:
  current $I_P$ flowing through the PZT during successive oscillation cycles; the corresponding output voltage $V_{Cp}$ across the internal capacitor $C_p$ of the PZT; and
  current $I_D$ flowing through diode 60, which is the current applied to intermediate capacitor 50 that will be used to charge the microbattery 44 and power the various electronic circuits and sensors of the implant.

The maximum output voltage $V_{DC}$ that it is possible to obtain is equal to the maximum open-circuit voltage $V_{OC}$ across the PZT, reduced by the drops of voltage $V_D$ across the diodes in series between the PZT and the intermediate capacitor 50, including the diodes of the full-bridge rectifier of interface 52 (i.e. the two diodes of the diode bridge that are in conduction state during a given alternation). After the zero-crossing of the current $I_P$ output by the PZT (at time $t_0$), diode 60 does not enter into conduction before a time $t_R$ corresponding to the time required for the voltage across the PZT internal capacitor $C_p$ to switch from ($V_{OC}+2V_D$) to $-(V_{OC}+2V_D)$. When the voltage $V_{DC}$ across the intermediate capacitor 50 increases, this time duration $t_R$ increases, and the conduction time $t_C$ correspondingly decreases.

As a matter of fact, at the beginning of a cycle for the first oscillations of the PZT after a heart beat, the conduction time is relatively long but, on the other hand, the voltage $V_{DC}$ accumulated on intermediate capacitor 50 is low, whereas, at the end of the cardiac cycle, the conduction time is relatively short but, on the other hand, the voltage $V_{DC}$ accumulated on intermediate capacitor 50 is far higher.

The optimum extraction of the energy is hence not in these extreme states, but in an intermediate state, which has to be determined to define a set point of the MPPT feedback control.

Figure 10:
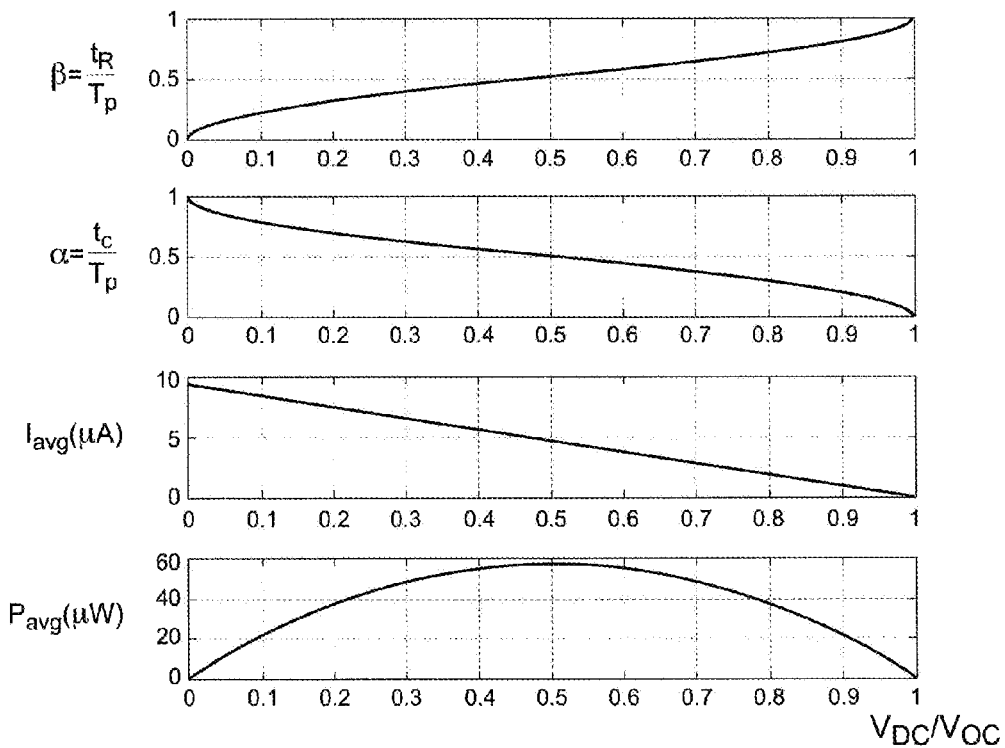
FIG. 10 illustrates the variations of the reverse and direct duty cycles as a function of the ratio between the open-circuit voltage of the PZT and the useful voltage outputted, as well as the corresponding variations of the mean current outputted as well as the output power extracted.

FIG. 10 shows various curves that illustrate, in particular, the existing relation between the variations of the direct duty cycle $\alpha$ or reverse duty cycle $\beta$ and the extracted mean power $P_{avg}$. These variations are given as a function of the ratio $V_{DC}/V_{OC}$ between the effective voltage $V_{DC}$ available at the output for charging the intermediate capacitor 50 and the maximum open-circuit voltage $V_{OC}$ that the PZT can provide between its terminals. It is demonstrated that, if the voltage drop across diode 60 is neglected, the power extracted from the PZT goes through a maximum for duty cycle values $\alpha = 0.5$ (or $\beta = 0.5$), that is to say when the output voltage $V_{DC}$ is equal to half the maximum open-circuit voltage $V_{OC}$ across the PZT.

If taking into account the voltage drops of the diodes of the circuit, as well as the offset and hysteresis introduced by the comparator circuit 62, the optimum is found to be in reality at a value slightly lower than 0.5 $V_{OC}$, corresponding to a direct duty cycle $\alpha$ slightly higher than 50% (or a reverse duty cycle $\beta$ slightly lower than 50%).

Concretely, the optimum can be around $\alpha = 53\%$, i.e. in a range $\alpha = 50$-$55\%$ (or around $\beta = 47\%$, i.e. a range $\beta = 45$-$50\%$).

Those optimum values correspond to the case, indicated hereinabove, of an interface 52 implementing a simple diode-bridge FBR.

They are to be adapted, theoretically or experimentally, if other interface circuit schemes are used.

Figure 11:
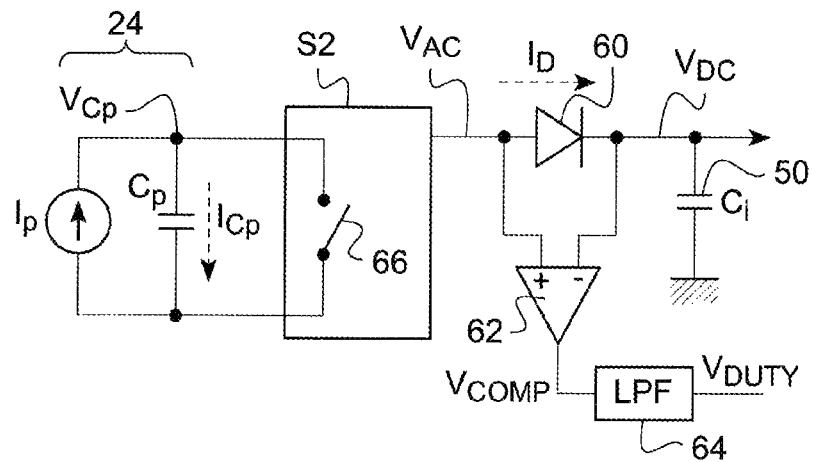
FIG. 11 is similar to FIG. 7, for an interface circuit of the FBR-SO type.
Figure 12:
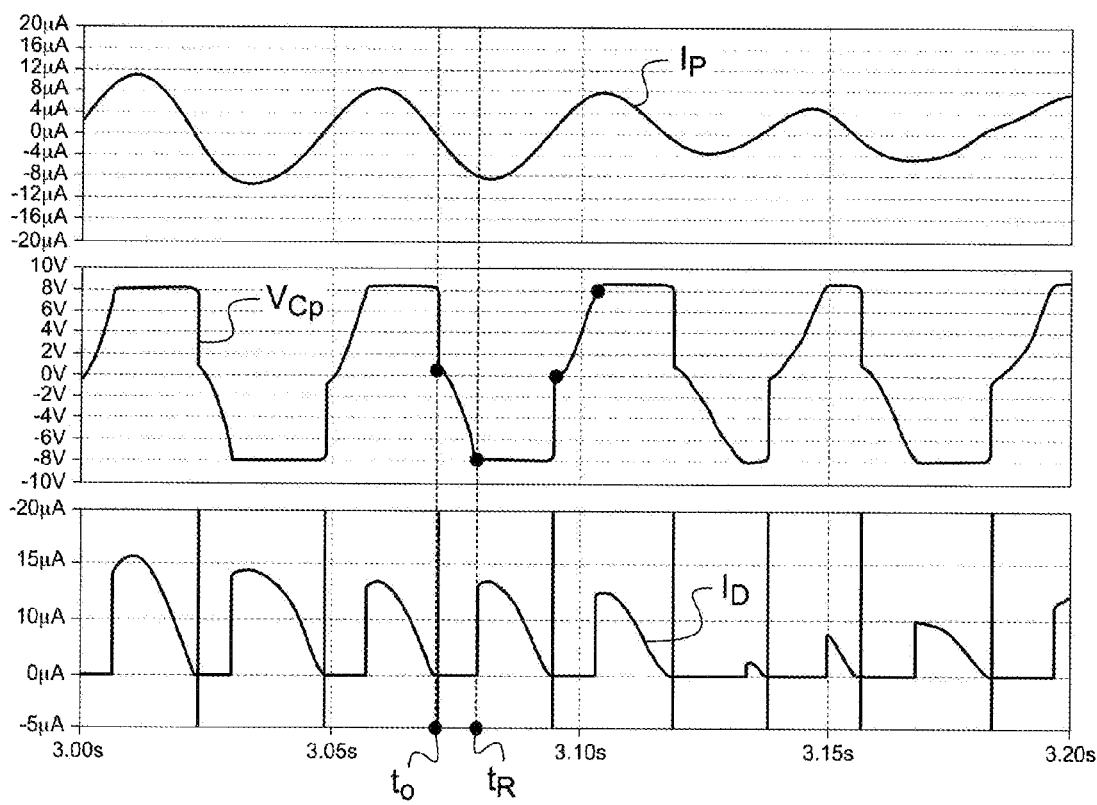
FIG. 12 illustrates the instantaneous variations of various electrical values and signals of the circuit of FIG. 11.

Hence, as illustrated in FIG. 11, the interface can be a circuit of the FBR-Switch Only (FBR-SO) type, i.e. an FBR circuit completed by a short-circuit switch 66 connected in parallel to the PZT and that closes when the current crosses zero, in order to discharge immediately the PZT internal capacitor. The corresponding variations of $I_P$, $V_{Cp}$ and $I_D$ are illustrated in FIG. 12.

Due to the closing of the switch 66, the open-circuit voltage $V_{OC}$ is doubled with respect to a simple FBR circuit, which changes the time $t_R$ before the diode enters into conduction. If taking into account the characteristics of the diodes used and the delay introduced by the detection of the zero-crossing (which requires an additional circuit), the optimum duty cycle is then in practice in a range $\alpha = 50$-$52\%$ (i.e. $\beta = 48$-$50\%$).

Figure 13:
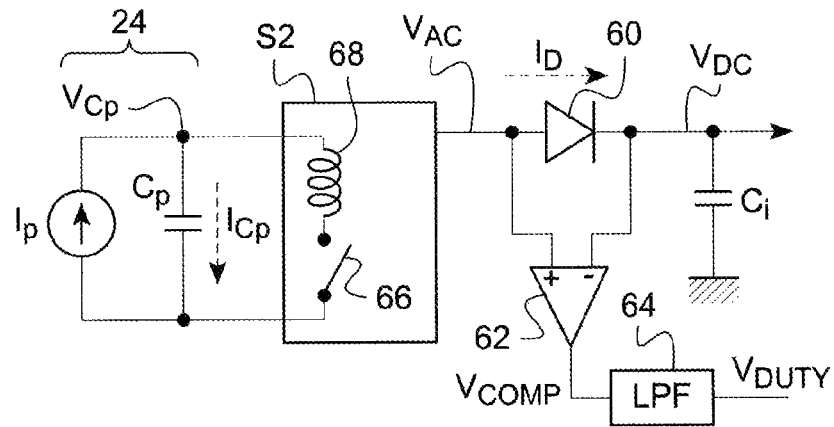
FIG. 13 is similar to FIG. 7, for an interface circuit of the P-SSHI type.
Figure 14:
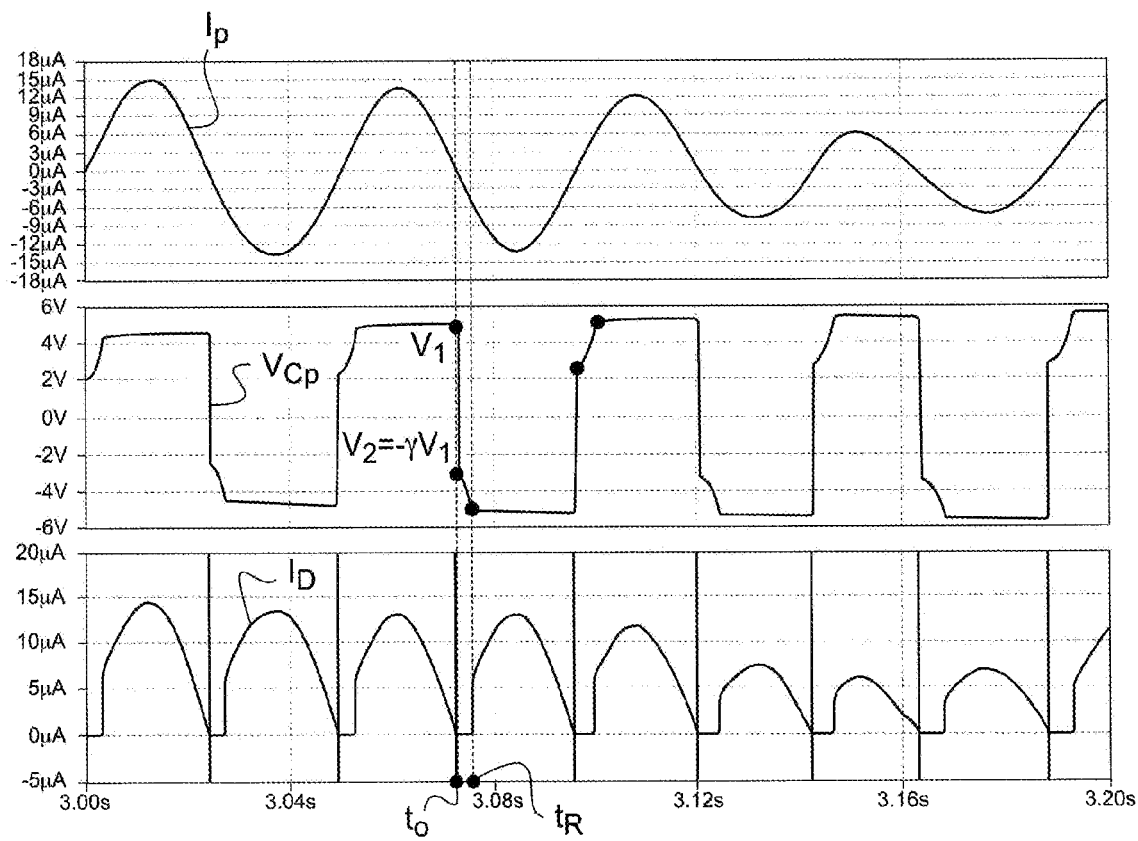
FIG. 14 illustrates the instantaneous variations of various electrical value and signals of the circuit of FIG. 13.

Another usable interface circuit is a circuit of the P-SSHI type mentioned hereinabove, which is essentially, as illustrated in FIG. 13, a circuit of the FBR-SO type in which an inductor 68 has been added in series with the short-circuit switch 66 connected across the PZT. The corresponding variations of $I_P$, $V_{Cp}$ and $I_D$ are illustrated in FIG. 14.

In practice, with such a P-SSHI interface circuit, the optimum duty cycle is in a range $\alpha = 52$-$60\%$ (i.e. $\beta = 40$-$48\%$).

Hence, as can be seen, although the theoretical optimum duty cycle is in any case of 50%, taking into account the various practical considerations related to the configuration chosen for the interface circuit and to the hardware components implemented, the real optimum duty cycle, although being around 50%, can be in a neighbor, but different, range of this theoretical value.

Examples of Circuits for Extracting a Duty Cycle Signal

Figure 15:
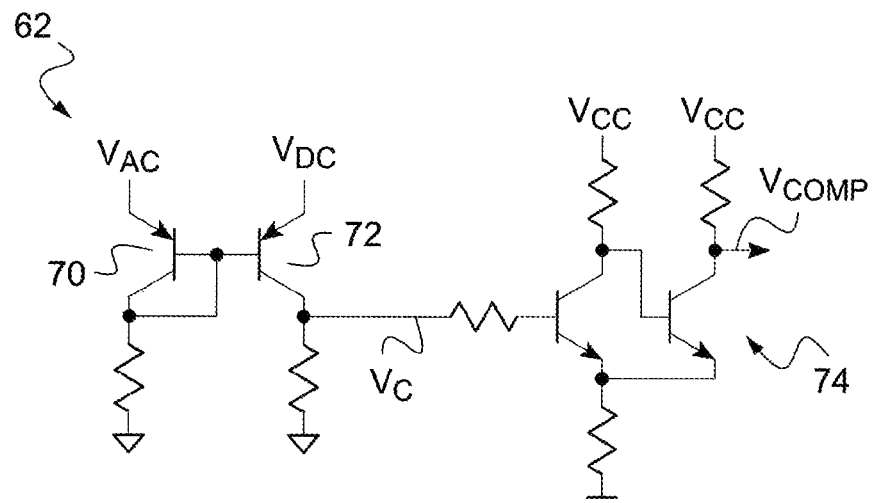
FIG. 15 is an exemplary embodiment of the comparator stage of the circuit of FIG. 7, 11 or 13.

FIG. 15 is an exemplary embodiment of the comparator stage 62 of the circuit of FIG. 7, 11 or 13.

This comparator is made as a self-powered circuit with two bipolar transistors 70, 72 arranged in opposition and receiving on their respective transmitters the signals $V_{AC}$ and $V_{DC}$ collected across diode 60. To obtain a binary signal $V_{COMP}$ representative of the cyclic conduction ratio (duty cycle) of diode 60, a Schmitt trigger stage 74 is coupled to the output of comparator 70, 72 so as to cause a saturation or "clamping" of signal $V_C$.

Figure 16:
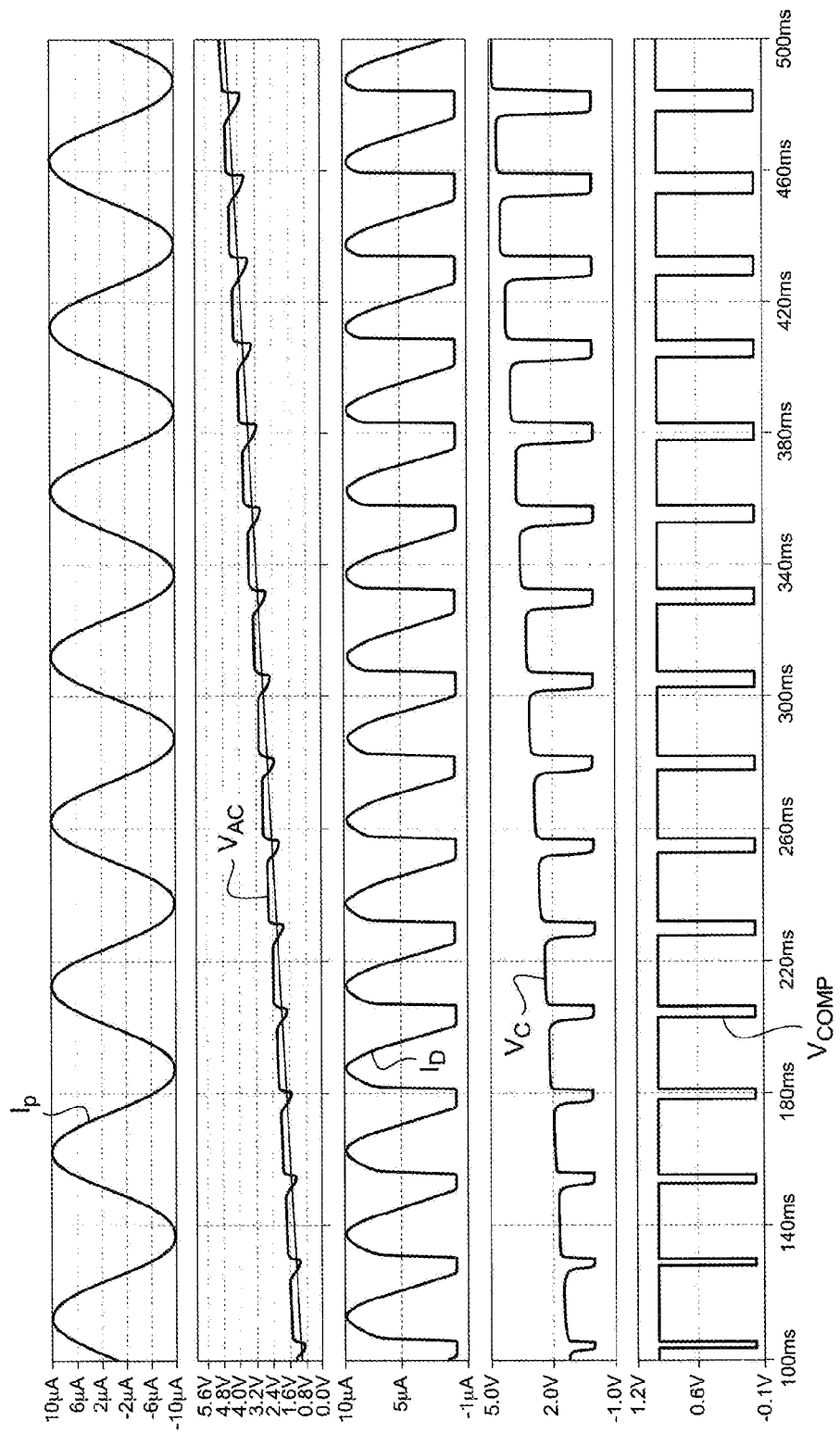
FIG. 16 illustrates various waveforms taken on the circuit of FIG. 7, implemented with the comparator stage structure of FIG. 15.

FIG. 16 illustrates, on five chronograms, the respective concomitant variations of (i) of the current $I_P$ output by the PZT, (ii) the output voltage $V_{AC}$ of interface circuit 52, (iii) the current $I_D$ flowing through diode 60, (iv) the output current $V_C$ of the pair of transistors 70, 72, and (v) the duty cycle signal $V_{COMP}$ output by the Schmitt trigger 74. It can be seen that, over the successive cycles of oscillation of the beam, the maximum amplitude of signal $V_C$ increases progressively, proportionally to the mean value of voltage $V_{AC}$, Schmitt trigger 74 outputting a binary signal $V_{COMP}$ representative of the duty ratio of diode 60.

Figure 17:
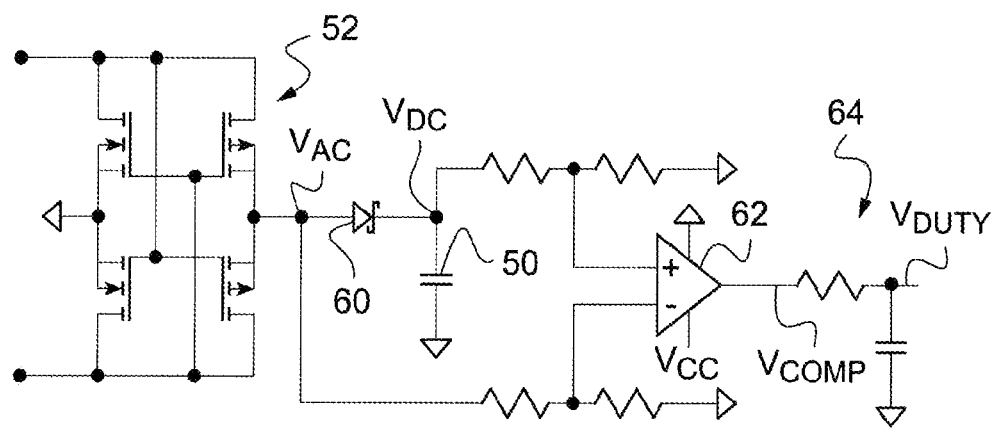
FIG. 17 is another exemplary embodiment of the comparator stage of the circuit of FIG. 7, 11 or 13.

FIG. 17 illustrates another exemplary practical embodiment of the comparator stage of FIG. 7, 11 or 13.

This example implements a single comparator component 62, using an external power supply $V_{CC}$. This comparator can be incorporated to a CMOS ASIC, or made from discrete COTS (Commercial Off-The-Shelf) PMOS/NMOS transistor components of a known type, which have, with respect to bipolar transistors, the advantage not to oppose a diode threshold voltage, hence having neither dead area nor significant charge loss. At the input of comparator 62, voltage dividers limit the voltage levels applied to the inputs of the comparator circuit to levels not exceeding the power supply voltage $V_{CC}$.

In this same FIG. 17 is also illustrated another alternative, usable independently of the type of comparator stage used, in which, to obtain the positive rectified voltage $V_{AC}$ from the signal output by the PZT, interface stage 52 is made as a negative voltage converter NVC instead of a diode bride. The NVC is made from MOSFET, which avoids the drawbacks of a diode bridge, in particular the direct voltage drop of the diodes when the latter are in conductive state, hence leading to a better efficiency of the interface circuit.

The MOSFET-based NVC arrangement includes no blocking diode. That is why it is followed by a passive or active diode to prevent a return of current from the capacitor $C_i$ to the PZT.

Figure 26:
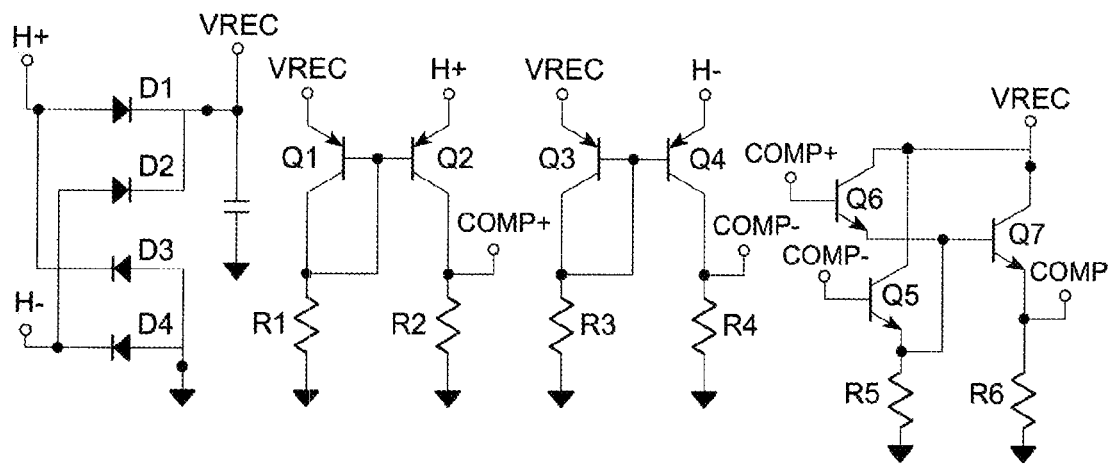
FIG. 26 illustrates an alternative embodiment of blocking diode and comparator interface circuit.

FIG. 26 shows another alternative in which interface circuit 52 is a four-diode rectifier, with two blocking diodes D1 and D2. The comparator that serves to estimate the duty cycle is consisted of two comparators with the outputs COMP+ and COMP−. A logical OR circuit makes it possible to combine the outputs of both comparators to form a signal COMP representative of the conduction of the two diodes D1 or D2, usable to estimate the duty cycle.

Examples of MPPT Loop Controlled by the Duty Cycle

Reference will now be made to FIGS. 18 to 25 to describe the principle of the MPPT feedback control implemented, according to the teachings of the present invention, based of the duty cycle, direct or reverse, determined by circuits such as those of FIG. 7, 11 or 13 described hereinabove.

Figure 18:
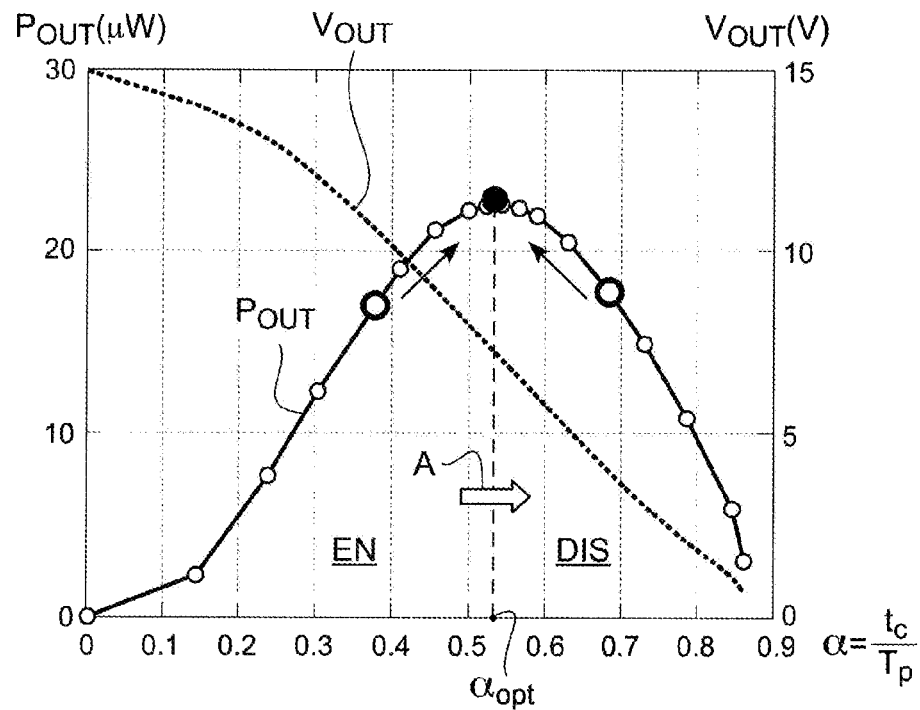
FIG. 18 schematically illustrates the principle of the MPPT feedback control implemented by the present invention, showing the respective variations, as a function of the direct duty cycle determined by circuits such as those of FIG. 7, 11 or 13, of the voltage outputted by the PEH and of the corresponding power extracted from the PZT.

In FIG. 18 is schematically illustrated the principle of an MPPT feedback control operating as a function of the direct duty cycle $\alpha = t_C/T_P$, the figure showing the variations of the output voltage $V_{out}$ output by the PEH and of the corresponding extracted power $P_{out}$, as a function of the variations of the direct duty cycle $\alpha$.

The matter is to control the system based on an optimum duty cycle value $\alpha_{opt}$ determined in advance, which is for example in a range of 50 to 55% for an interface of the FBR or FBR-SO type, or of 50 to 60% for an interface of the SSHI type, as explained hereinabove.

When the current instantaneous value of the duty cycle $\alpha$, as measured by the signal $V_{DUTY}$, is higher than the optimum value $\alpha_{opt}$, the feedback control disables converter 54, which has for effect to allow the output voltage $V_{DC}$ to increase the electric charge of intermediate capacitor 50. This situation corresponds to an operating point located, in FIG. 18, in the DIS (disable) area, on the right of the optimum operating point $\alpha_{opt}$.

On the reverse, when the instantaneous current value of the duty cycle is lower than the optimum value $\alpha_{opt}$, converter 54 is enabled for extracting the energy accumulated in intermediate capacitor 50, and transferring this energy to the microbattery 44 and to the various application circuits of the device. This situation corresponds to an operating point located, in FIG. 18, in the EN (enabled) area, on the left of the optimum operating point $\alpha_{opt}$.

The extraction of energy from intermediate capacitor 50 by converter 54 will cause a progressive increase of the duty cycle $\alpha$ and a decrease of the PZT output voltage $V_{out}$; when $\alpha$ exceeds the limit $\alpha_{opt}$, the converter is then disabled (arrow A), with reverse effects and, consequently, holding of the duty cycle, and hence of the power $P_{out}$ extracted from the beam, around the optimum operating point.

Figure 19:
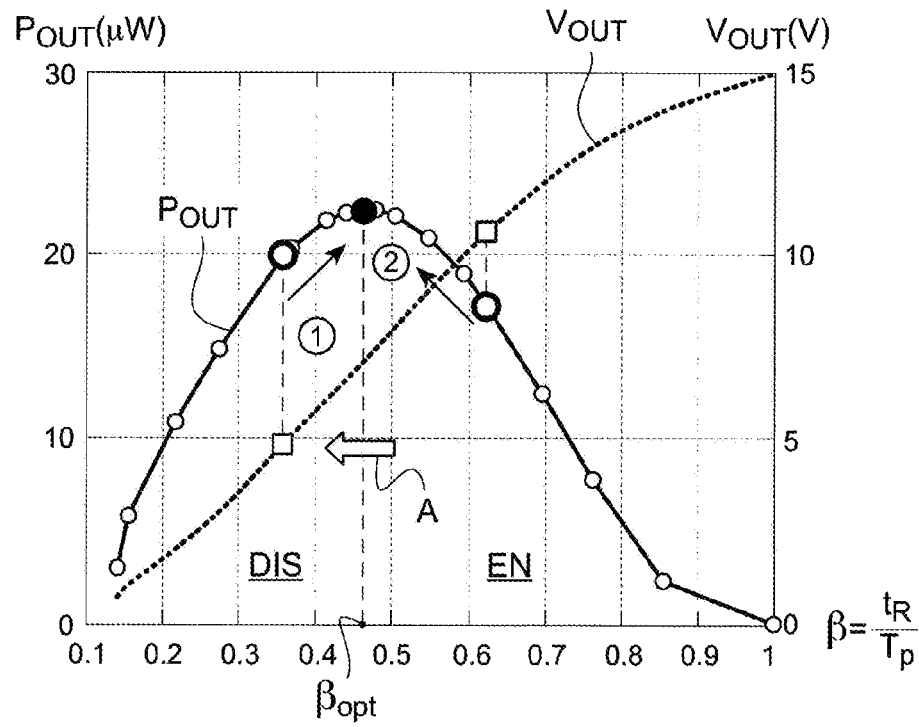
FIG. 19 is similar to FIG. 18, as a function of the variations of the reverse duty cycle.

FIG. 19 is similar to FIG. 18, for variations of the reverse duty cycle $\beta = t_R/T_P$.

This hypothesis corresponds to the case in which the comparator across diode 60 is configured to produce a high signal when the diode is not conductive. The MPPT feedback control operating mode is comparable to that exposed hereinabove, mutatis mutandis, for a holding of the operating point around the optimum value $\beta_{opt}$.

Figure 20:
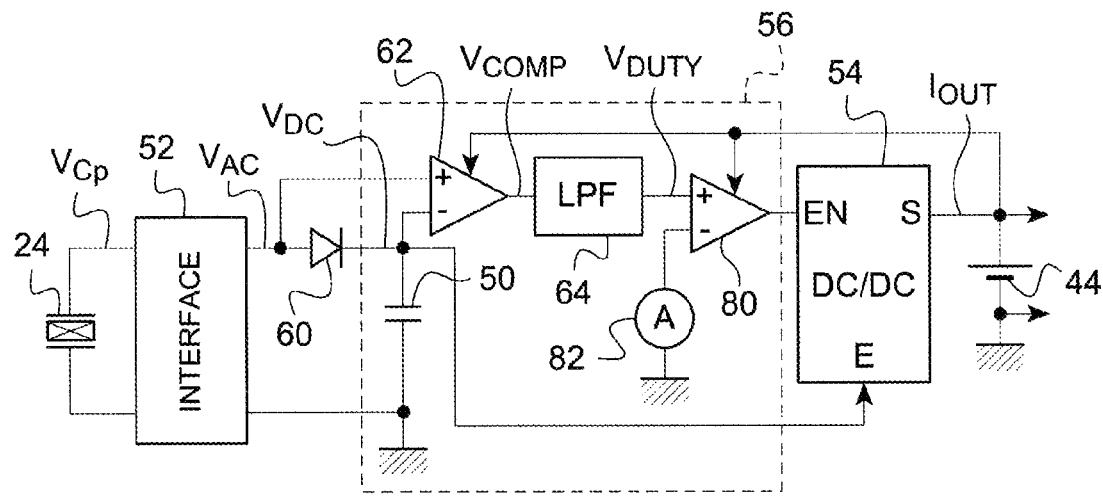
FIG. 20 illustrates a first set of PEH circuits implementing the teachings of the invention, with an MPPT feedback control loop controlled by the variations of the reverse duty cycle.
Figure 22:
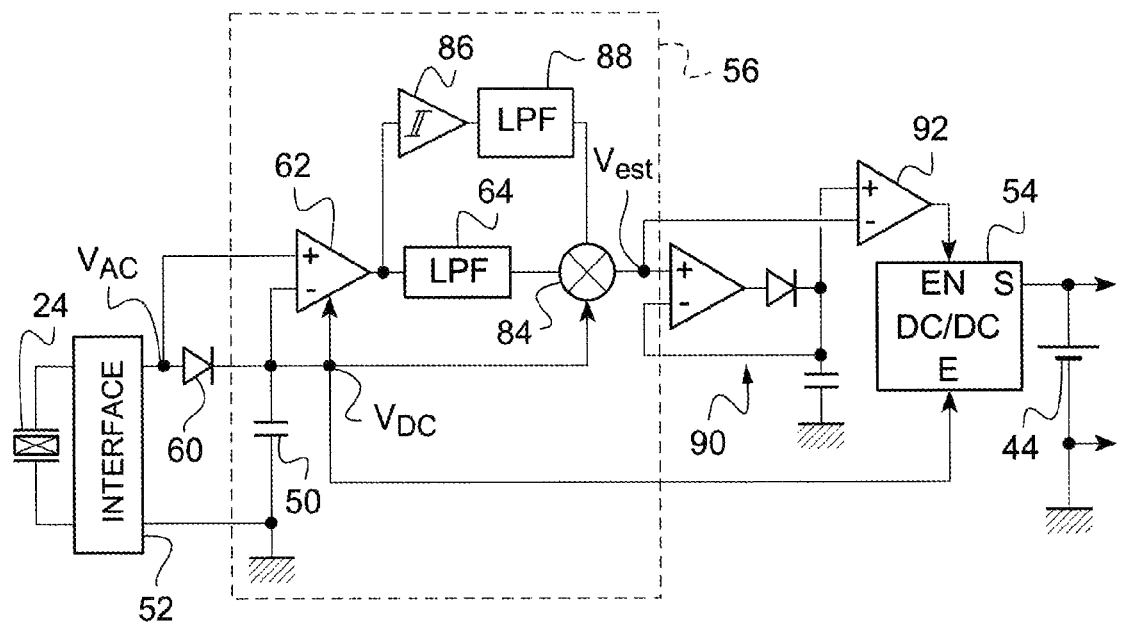
FIG. 22 is similar to FIG. 20, for circuits adapted to a preexisting power supply stage of a known type already comprising a maximum power searching stage, this stage being then controlled by the variations of the direct duty cycle.
Figure 21:
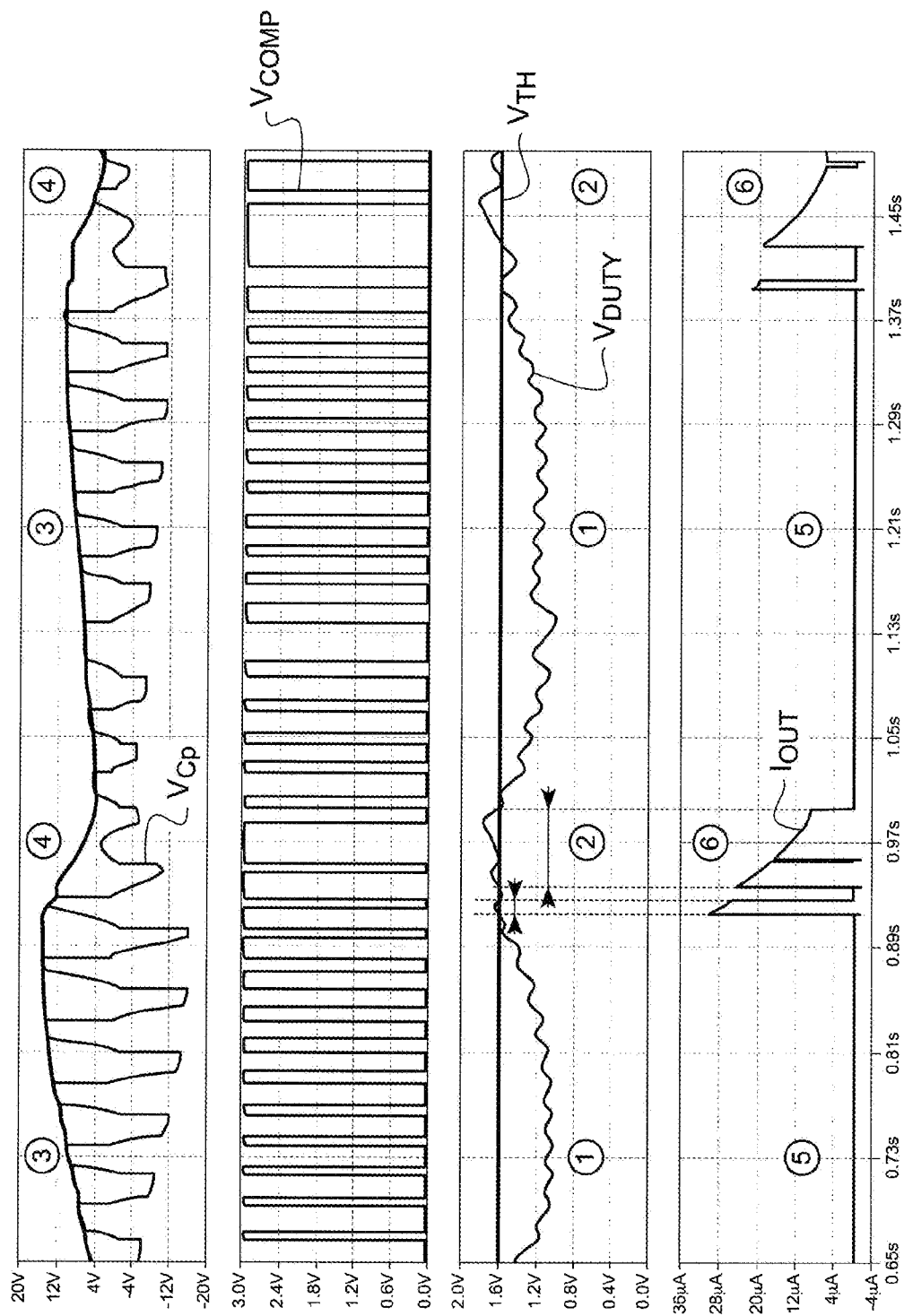
FIG. 21 is a sequence of chronograms showing the instantaneous variations of various signals produced by the circuits of FIG. 20 during two successive oscillations of the PZT.

FIGS. 20, 22 and 24 illustrate three examples of PEH circuitry implementing the teachings of the invention exposed hereinabove, with an MPPT feedback control loop controlled by the variations of the duty cycle. FIG. 20 illustrates a first example of PEH circuitry, with an MPPT feedback control loop controlled by the variations of the reverse duty cycle $\beta$. FIG. 21 illustrates the instantaneous variations of various signals produced by this circuitry during two successive oscillations of the PZT. The PZT 24 outputs a variable voltage $V_{Cp}$ (first chronogram of FIG. 21) that is applied to interface circuit 52, which is of one of the mentioned hereinabove types (FBR, FBR-SO, P-SSHI) or other; the alternating voltage $V_{AC}$ output of this circuit is rectified by diode 60 to provide a rectified voltage $V_{DC}$ applied to the intermediate buffer capacitor 50. MPPT rectifier stage 56 comprises comparator 62, whose respective inputs are connected to the terminals of diode 60 and that, as described hereinabove with reference to FIG. 7, outputs a signal $V_{COMP}$ (second chronogram of FIG. 21) applied to the low-pass filter LPF 64 to give the filtered signal $V_{DUTY}$ (third chronogram of FIG. 21) representative of the variations of the duty cycle of the conduction periods across diode 60. In the configuration illustrated, comparator 62 outputs a high level signal when the diode is not conductive, so that the signal $V_{DUTY}$ is a signal representative of the reverse duty cycle $\beta$ (if a signal representative of the direct duty cycle $\alpha$ is desired, the inputs of comparator 62 have just to be inverted).

The signal $V_{DUTY}$ is applied to one of the inputs of a second comparator 80, whose other input is connected to a generator 82 for generating a threshold value voltage $V_{TH}$. The output of comparator 80 is applied to the EN (enable) input of converter 54. This converter 54, when enabled, converts the voltage across capacitor 50, applied to input E, into a regulated voltage, provided at output S, making it possible to ensure, by a current $I_{out}$ (fourth chronogram of FIG. 21) the charging of microbattery 44 and the powering of the various application circuits of the implant located downstream.

The operation of this feedback control is the following: at the beginning of the cycle, the voltage across capacitor 50 is relatively low and the reverse duty cycle β is relatively small. After a few cycles of vibration of the PZT, this voltage increases and the βs decrease: cf. areas denoted ① and ③ in FIGS. 19 and 21.

When β reaches a predetermined threshold (β=β$_{opt}$+Δ, with a value Δ of 5 to 10%), corresponding to the crossing of the reference $V_{TH}$ by the signal $V_{DUTY}$ (as illustrated in the third chronogram of FIG. 21), then converter 54 is enabled (area denoted ② in FIGS. 19 and 21).

The enabling of converter 54 has for effect to extract the charges accumulated by capacitor 50, which has for consequence to reduce the voltage across the latter (arrow A in FIG. 19 and area denoted ④ in FIG. 21). The energy extracted from the capacitor, applied to input E of converter 54, is regulated and transferred on output S to microbattery 44 and to the downstream application circuits (area ⑥ in FIG. 21). The enabling of converter 54 lasts until the duty cycle β falls below the threshold value ($V_{DUTY}$<$V_{TH}$). Converter 54 is then disabled, which makes it possible to restart a cycle of charge of capacitor 50, with correspondingly a progressive increase of the duty cycle β, close to its threshold value. Contrary to the usual indications in the literature that, in order to have a stable voltage at the converter output, prescribe to use, for the buffer capacitor, a component of value much higher than the PZT internal capacitance (at least 100 to 1000 times higher), in the case the present invention it is preferable to use a buffer capacitor of low value—typically 10 to 20 times only the value of the PZT internal capacitance—in order to be able to ensure a fast feedback control of the MPPT loop that maximizes the output voltage, and therefore the power extracted from the PZT.

The above-described circuit of FIG. 20 allows a feedback control of the power extracted from the PEH without thereby estimating directly this power. It is sometimes desirable to provide an indicator correlated with the power and to use a preexisting MPPT circuit to perform the feedback control. FIGS. 22 and 24 describe a change of the circuit of FIG. 20 to provide such an indicator of the extracted power.

FIG. 22 illustrates a second example of PEH circuitry, adapted to a preexisting power supply stage of a known type, already comprising a maximum power searching stage, implementing in particular an envelop detector.

The MPPT feedback control stage 56 comprises an analog multiplier 84, one of the inputs of which receives the output signal of the comparator 62/low-pass filter 64 unit described hereinabove. This input hence receives a signal proportional to the product $V_{DC}\cdot\alpha$. The other input of the multiplier is connected to a branch comprising a clamping stage 86 whose input is connected to the output of comparator 62 and whose output is connected to a second low-pass filter 88. This other input of the multiplier hence receives a signal proportional to α. The multiplier output provides a signal proportional to $K(V_{DC}\cdot\alpha)\alpha$, which is representative of an estimate of the second order around α=0 of the power. This signal can be used with preexisting feedback control circuits operating on the basis of an input signal of the "estimated power" type. It can in particular be circuits comprising an MPPT envelope detector 90, receiving signal $V_{est}$ at the output of multiplier 90, associated with an MPPT comparator 92, whose output controls the enable input EN of converter 54 (wherein circuits 90, 92 can be, in certain components, already integrated to the other circuits of converter 54).

FIG. 23, which shows the effectively measured extracted power $P_{out}$ and the estimate signal $V_{est}$ provided by stage 56, exhibits an excellent correlation, in the vicinity of the maximum of the curve, between the estimate of the power and the really extracted power.

FIG. 24 illustrates an alternative of the PEH circuitry of FIG. 22, in which the analog multiplier 84 receives directly, on one of its inputs, the rectified voltage $V_{DC}$ of buffer capacitor 50, and on its other input, the output signal of a second comparator 94, an input of which is connected to the comparator 62/low-pass filter 64 unit and the other input of which is connected to a reference voltage generator 96. The first input hence receives a signal proportional to $V_{DC}$, whereas the second input receives a signal proportional to K(α−B), with B an offset equal to B=½−1/π=0, 182. Multiplier 84 hence provides a signal $V_{est}$ proportional to K(α−B)×$V_{DC}$, representative of the product I×V (current×voltage). Indeed, it is shown that, in an approximation of the first order around the optimum value, the mean current produced varies linearly as a function of the term α−B.

Figure 25:
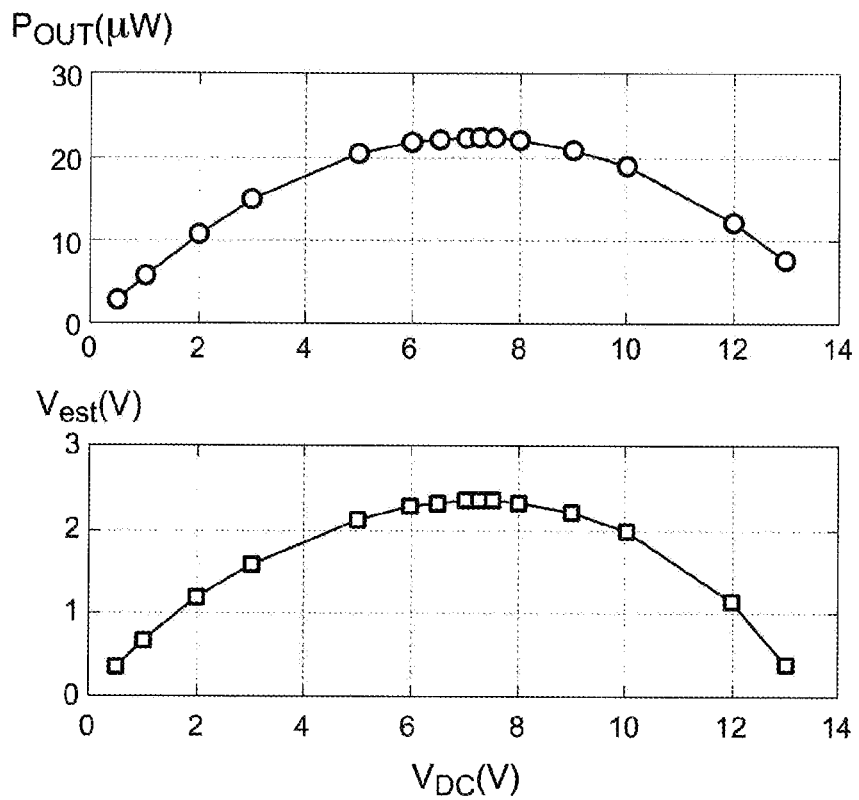
FIG. 25 is similar to FIG. 23, for curves obtained with the circuits of FIG. 24.

Here again, as illustrated in FIG. 25, which is similar to FIG. 23 for the circuit of FIG. 24, it is observed, in the vicinity of the maximum of the curve, an excellent correlation between the power really extracted $P_{out}$ and the estimate $V_{est}$ of this power, produced by the MPPT stage 56.

Advantages Provided by the Invention

The just-exposed solution of the invention has, compared to the already proposed circuits, the following advantages:
- "free" MPPT regulation, i.e. based on the observation of signals already available on the interface circuit; it is hence not necessary to make the system operate out of its optimum area, as in the case of the MPPT algorithms of the P&O or FOC type, nor to perform a complex operation such as calculating a product V×I;
- fast response: a single cycle of vibration of the PEH is sufficient to determine whether it is necessary to change the output voltage, i.e. a response time of the order of 25 ms for a PZT whose natural frequency is 20 Hz; this advantage is particularly precious in the case of an application to a pacemaker, where the cycles of vibration of the PZT (25 ms) are far shorter than the cardiac cycles (500 to 1000 ms) at the origin of the vibrations of the inertial unit;
- simplicity of the circuitry, which can be implemented with simple analog circuits, incorporated to an ASIC, or made from COTS (Commercial Off-The-Shelf) components, with a very low energy consumption, suitable for very demanding applications in terms of energy balance, such as the cardiac implants;
- maximization of the power transferred from the PEH to the intermediate capacitor in a manner fully independent of the performances of the DC/DC converter arranged downstream from this intermediate capacitor.
- implementation of the invention with any known technology of DC/DC converter, without changing the latter.

The invention claimed is:

1. An energy harvesting module, comprising:
   a pendular unit subjected to external stresses applied to the module, the pendular unit comprising a beam that is elastically deformable in bending according to at least one degree of freedom, with a clamped end and an opposite free end coupled to an inertial mass,
  wherein the beam is a piezoelectric beam forming a mechanical-electrical transducer adapted to convert a mechanical energy produced by oscillations of the pendular unit into an oscillating alternating electrical signal collected by electrodes of the beam; and
a power management circuit, adapted to rectify and regulate the signal collected by the electrodes, whereby outputting a stabilized power supply direct voltage or current,
wherein the power management circuit comprises:
an interface circuit coupled to the piezoelectric beam, receiving as an input the oscillating alternating electrical signal provided by the piezoelectric beam and outputting a rectified signal comprising a sequence of pulses at a frequency equal to a multiple of the oscillation frequency of the pendular unit;
at the output of the interface circuit, a buffer capacitor charged by successive pulses provided by the interface circuit;
a converter regulator adapted to convert a buffer capacitor discharge current into said stabilized power supply direct voltage or current; and
a circuit for controlling the converter regulator, comprising a feedback control stage of the Maximum Power-Point Tracking, MPPT, type, based on an estimate of a power extracted from the piezoelectric beam,
and wherein the MPPT feedback control stage is controlled by a current value of a direct or reverse duty cycle of the pulses outputted at a frequency equal to a multiple of the oscillation frequency of the pendular unit at the output of the interface circuit.

2. The module of claim 1, wherein:
the power management circuit further comprises a blocking diode interposed between the interface circuit and the buffer capacitor, and
the MPPT feedback control stage comprises:
  a circuit for detecting conduction periods of the blocking diode;
  an extraction circuit adapted to produce a signal representative of a current value of the duty cycle based on conduction and non-conduction periods detected by the detection circuit; and
  a circuit for comparing the current value of the duty cycle with a predetermined optimum duty cycle value.

3. The module of claim 2, wherein the MPPT feedback control stage further comprises a control circuit, for:
  if the current duty cycle value is higher than the optimum duty cycle value, coupling the buffer capacitor to the converter regulator so as to discharge the buffer capacitor towards an input of the converter regulator, or
  if the current duty cycle value is lower than the optimum duty cycle value, uncoupling the buffer capacitor from the converter regulator so as to allow the charging of the buffer capacitor by the successive pulses outputted by the interface circuit to continue.

4. The module of claim 3, wherein the converter regulator is a step-up/step-down switching regulator of the buck-boost type, which can be selectively enabled/disabled by the control circuit.

5. The module of claim 2, wherein the conduction period detection circuit and the extraction circuit comprise a comparator coupled at an input to the blocking diode, adapted to detect the polarity of the potential difference across the blocking diode and, downstream from the comparator, a low-pass filter outputting a signal representative of the current duty cycle value.

6. The module of claim 2, wherein the interface circuit comprises a full-bridge rectifier, FBR, circuit, with a diode bridge or a MOSFET-based negative voltage converter, NVC, and the predetermined optimum duty cycle value is between 50% and 55% in terms of direct duty cycle, or between 45% and 50% in terms of reverse duty cycle.

7. The module of claim 2, wherein the interface circuit comprises a synchronized discharge switching FBR circuit, FBR-SO, and the predetermined optimum duty cycle value is between 50% and 52% in terms of direct duty cycle, or between 48% and 50% in terms of reverse duty cycle.

8. The module of claim 2, wherein the interface circuit comprises a synchronized parallel discharge inductor switching FBR circuit, P-SSHI, and the predetermined optimum duty cycle value is between 52% and 60% in terms of direct duty cycle, or between 40% and 48% in terms of reverse duty cycle.

9. The module of claim 2, wherein the MPPT feedback control stage comprises:
  a first comparator comparing voltages across the blocking diode;
  downstream from the first comparator, a low-pass filter outputting a signal representative of a current value of the reverse duty cycle; and
  a second comparator comparing a signal output by the low-pass filter with a voltage reference, and outputting a signal for controlling the converter regulator.

10. The module of claim 2, wherein the MPPT feedback control stage comprises:
  a first comparator comparing voltages across the blocking diode;
  downstream from the first comparator, a first low-pass filter outputting a first signal representative of a current value of the direct duty cycle and of a voltage outputted by the interface circuit;
  a Schmitt trigger receiving the signal outputted by the first comparator;
  downstream from the Schmitt trigger, a second low-pass filter outputting a second signal representative of a current value of the direct duty cycle; and
  a multiplier combining the signals outputted by the first and the second low-pass filters, respectively, and outputting a signal representative of an estimate of a power extracted from the piezoelectric beam.

11. The module of claim 2, wherein the MPPT feedback control stage comprises:
  a first comparator comparing voltages across the blocking diode;
  downstream from the first comparator, a low-pass filter outputting a first signal representative of a current duty cycle value and of a level of a voltage outputted by the interface circuit;
  downstream from the low-pass filter, a second comparator comparing the signal outputted by the low-pass filter with a voltage reference, and outputting a signal that is function, but with an offset, of a current value of the direct duty cycle; and
  a multiplier combining the signal outputted by the second comparator and a voltage signal across the buffer capacitor, and outputting a signal representative of an estimate of a power extracted from the piezoelectric beam.

12. The module of claim 10, further comprising an envelope detector receiving as an input the signal representative of an estimate of the power extracted from the piezoelectric beam, outputted by the multiplier.

13. The module of claim 1,
wherein the module is incorporated to an autonomous device including within a device body: an electronic unit; said power harvesting module; and an energy storage component for powering the electronic unit,
and wherein said stabilized direct voltage or current provided by the power management circuit is used to power the electronic unit and/or to charge the energy storage component of the autonomous device.

14. The module of claim 13, wherein the autonomous device is an active medical device.

15. The module of claim 14,
wherein the active medical device is an implantable autonomous capsule comprising a capsule body provided with an anchoring element for anchoring it to a wall of a patient's organ,
and wherein said external stresses to which is subjected the pendular unit of the energy harvesting module are stresses applied to the capsule body under the effect of movements of said wall and/or blood flow rate variations in the surrounding environment.

16. The module of claim 11, further comprising an envelope detector receiving as an input the signal representative of an estimate of the power extracted from the piezoelectric beam, outputted by the multiplier.

\* \* \* \* \*